US012570622B2

(12) United States Patent
Hecht et al.

(10) Patent No.: US 12,570,622 B2
(45) Date of Patent: Mar. 10, 2026

(54) THERAPEUTIC COMPOUNDS

(71) Applicant: ARIZONA BOARD OF REGENTS ON BEHALF OF ARIZONA STATE UNIVERSITY, Scottsdale, AZ (US)

(72) Inventors: Sidney Hecht, Phoenix, AZ (US); Omar Khdour, Phoenix, AZ (US); Sandipan Roy Chowdhury, Tempe, AZ (US); Nishant P. Visavadiya, Tempe, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 529 days.

(21) Appl. No.: 18/070,993

(22) Filed: Nov. 29, 2022

(65) Prior Publication Data

US 2023/0295101 A1 Sep. 21, 2023

Related U.S. Application Data

(60) Continuation of application No. 16/924,763, filed on Jul. 9, 2020, now Pat. No. 11,560,360, which is a division of application No. 16/327,284, filed as application No. PCT/US2017/048482 on Aug. 24, 2017, now Pat. No. 10,745,366.

(60) Provisional application No. 62/379,654, filed on Aug. 25, 2016.

(51) Int. Cl.

| | |
|---|---|
| ***C07D 279/14*** | (2006.01) |
| ***A61K 31/5415*** | (2006.01) |
| ***A61P 3/10*** | (2006.01) |
| ***A61P 9/00*** | (2006.01) |
| ***A61P 25/28*** | (2006.01) |
| ***A61P 35/00*** | (2006.01) |
| ***A61P 39/06*** | (2006.01) |
| ***C07D 279/18*** | (2006.01) |

(52) U.S. Cl.

CPC ........ *C07D 279/18* (2013.01); *A61K 31/5415* (2013.01); *A61P 3/10* (2018.01); *A61P 9/00* (2018.01); *A61P 25/28* (2018.01); *A61P 35/00* (2018.01); *A61P 39/06* (2018.01); *C07D 279/14* (2013.01)

(58) Field of Classification Search

CPC ........................... C07D 279/14; C07D 279/18; A61K 31/5415; A61P 39/06; A61P 25/28; A61P 9/00; A61P 3/10; A61P 35/00

See application file for complete search history.

(56) References Cited

U.S. PATENT DOCUMENTS

| | | | | |
|---|---|---|---|---|
| 4,667,032 | A | 5/1987 | Lau et al. | |
| 8,952,025 | B2 | 2/2015 | Hecht et al. | |
| 9,102,626 | B2 | 8/2015 | Hecht et al. | |
| 9,334,250 | B2 | 5/2016 | Chowdhury et al. | |
| 9,388,163 | B2 | 7/2016 | Hecht et al. | |
| 9,440,967 | B2 | 9/2016 | Hecht et al. | |
| 9,624,255 | B2 | 4/2017 | Hecht et al. | |
| 9,884,114 | B2 | 2/2018 | Chang et al. | |
| 9,919,055 | B2 | 3/2018 | Hecht et al. | |
| 9,957,214 | B2 | 5/2018 | Madathil et al. | |
| 10,046,068 | B2 | 8/2018 | Hecht et al. | |
| 10,364,227 | B2 | 7/2019 | Hecht et al. | |
| 10,745,366 | B2 | 8/2020 | Hecht et al. | |
| 11,560,360 | B2 | 1/2023 | Hecht et al. | |
| 2011/0293530 | A1 | 12/2011 | Hecht et al. | |
| 2012/0238543 | A1 | 9/2012 | Hurt et al. | |
| 2013/0266518 | A1 | 10/2013 | Hecht et al. | |
| 2013/0317012 | A1 | 11/2013 | Wischik et al. | |
| 2014/0038963 | A1 | 2/2014 | Hecht et al. | |
| 2015/0017201 | A1 | 1/2015 | Chang et al. | |
| 2016/0228491 | A1* | 8/2016 | Wilson ............... | A61K 31/5415 |
| 2018/0002709 | A1 | 1/2018 | Hecht et al. | |
| 2018/0065941 | A1 | 3/2018 | Hecht et al. | |
| 2018/0125969 | A1 | 5/2018 | Chang et al. | |
| 2018/0371526 | A1 | 12/2018 | Chen et al. | |

(Continued)

FOREIGN PATENT DOCUMENTS

| | | | |
|---|---|---|---|
| WO | 2010006153 | A2 | 1/2010 |
| WO | 2010062854 | A2 | 6/2010 |
| WO | 2011019419 | A1 | 2/2011 |

(Continued)

OTHER PUBLICATIONS

U.S. Appl. No. 16/327,287.

(Continued)

*Primary Examiner* — Erich A Leeser

(74) *Attorney, Agent, or Firm* — Viksnins Harris Padys Malen LLP

(57) ABSTRACT

The invention provides compounds having the general formula I:

I

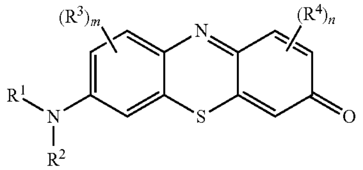

and pharmaceutically acceptable salts thereof, wherein the variables $R^1$, $R^2$, $R^3$, $R^4$, subscipt m and n, have the meaning as described herein, and compositions containing such compounds and methods for using such compounds and compositions.

20 Claims, 9 Drawing Sheets

(56) References Cited

U.S. PATENT DOCUMENTS

| | | | |
|---|---|---|---|
| 2019/0282706 A1 | 9/2019 | Chen et al. | |

FOREIGN PATENT DOCUMENTS

| | | | |
|---|---|---|---|
| WO | 2011103536 A1 | 8/2011 | |
| WO | 2012138713 A2 | 10/2012 | |
| WO | 2013120081 A1 | 8/2013 | |
| WO | 2014055629 A1 | 4/2014 | |
| WO | 2014059158 A1 | 4/2014 | |
| WO | 2014145109 A1 | 9/2014 | |
| WO | 2014145119 A1 | 9/2014 | |
| WO | 2014152718 A1 | 9/2014 | |
| WO | 2016118877 A1 | 7/2016 | |
| WO | 2016133995 A1 | 8/2016 | |
| WO | 2017200787 A1 | 11/2017 | |
| WO | 2017218537 A1 | 12/2017 | |
| WO | 2016133959 A9 | 2/2018 | |
| WO | 2018039077 A1 | 3/2018 | |

OTHER PUBLICATIONS

U.S. Appl. No. 16/310,305.

Acre, P , et al., “A Strategy for Suppressing Redox Stress within Mitochondria”, ACS Medicinal Chemistry Letters 2(8), 608-613 (2011).

Arce, P , et al., “Analysis of the structural and mechanistic factors in antioxidants that preserve mitochondrial function and confer cytoprotection”, Bioorganic & Medicinal Chemistry 20(17), 5188-5201 (2012).

Armstrong, J , et al., “Does Oxidative Stress Contribute to the Pathology of Friedreich’s Ataxia? A Radical Question”, FASEB J 24(7), 2152-2163 (2010).

Atamna, H , et al., “Methylene blue delays cellular senescence and enhances key mitochondrial biochemical pathways”, FASEB J 22(3), 703-712 (2008, available online 2007).

Baddeley, T , et al., “Complex Disposition of Methylthioninium Redox Forms Determines Efficacy in Tau Aggregation Inhibitor Therapy for Alzheimer’s Disease”, Journal of Pharmacology and Experimental Therapeutics 352(1), 110-118 (2015).

Barnham, K , et al., “Neurodegenerative diseases and oxidative stress”, Nat Rev Drug Discov 3(3), 205-214 (2004).

Bruchey, A , et al., “Behavioral, Physiological and Biochemical Hormetic Responses to the Autoxidizable Dye Methylene Blue”, American Journal of Pharmacology and Toxicology 3(1), 72-79 (2008).

Calabrese, V , et al., “Oxidative stress, mitochondrial dysfunction and cellular stress response in Friedreich’s ataxia”, J Neuro Sci 233(1-2), 145-162 (2005).

Chowdhury, S , et al., “Lipophilic methylene violet analogues as modulators of mitochondrial function and dysfunction”, Bioorganic & Medicinal Chemistry 25, 5537-5547 (2017).

Chowdhury, S , et al., “Synthesis and evaluation of methylene violet analogues as potential therapeutic agents for neurodegenerative and mitochondrial diseases”, Manuscript, 38 pages (2016).

Fash, D , “Effects of alkyl side chain modification of coenzyme Q10 on mitochondrial respiratory chain function and cytoprotection”, Bioorg Med Chem 21(8), 2346-2354 (2013).

Fiore, C , et al., “The mitochondrial ADP/ATP carrier: Structural, physiological and pathological aspects”, Biochimie 80(2), 137-150 (1998).

Frantz, M , et al., “Mitochondria as a target in treatment”, Environmental and Molecular Mutagenesis 51(5), 462-475 (2010).

Gaetani , “Catalase and glutathione peroxidase are equally active in detoxification of hydrogen peroxide in human erythrocytes”, Blood 73, 334-339 (1989).

Green, R , “A Report on Fifty Cases of Malaria Treated with Atebrin. A New Synthetic Drug”, The Lancet 219(5668), 826-829 (1932).

Heller, A , et al., “Targeting drugs to mitochondria”, European Journal of Pharmaceutics and Biopharmaceutics 82 (1), 1-18 (2012).

Henze, K, et al., “Evolutionary biology: essence of mitochondria”, Nature 426, 127-128 (2003).

Houghtaling, M , et al., “Photobiological Properties of Positively Charged Methylene Violet Analogs”, Photochemistry and Photobiology 71(1), 20-28 (2000).

Khdour, O , et al., “An Optimized Pyrimidinol Multifunctional Radical Quencher”, ACS Med Chem Lett 4(8), 724-729 (2013).

Lin, M , et al., “Mitochondrial dysfunction and oxidative stress in neurodegenerative diseases”, Nature 443(7113), 787-795 (2006).

Loeb, R , et al., “Activity of a New Antimalarial Agent, Chloroquine (SN 7618)”, JAMA 130(16), 1069-1070 (1946).

Markesbery , et al., “Oxidative alterations in Alzheimer’s disease”, Brain Pathology 9(1), 133-146 (1999).

Mates, J , et al., “Antioxidant enzymes and human diseases”, Clin Biochem 32, 595-603 (1999).

Matsuno-Yagi , et al., “Studies on the mechanism of oxidative phosphorylation: Catalytic site cooperativity in ATP synthesis”, J. Biol. Chem. 260(27), 14424-14427 (1985).

Melis, V , et al., “Effects of oxidized and reduced forms of methylthioninium in two transgenic mouse tauopathy models”, Behavioral Pharmacology 26(4), 353-368 (2015).

Murphy, M , “How mitochondria produce reactive oxygen species”, Biochem J 417(1), 1-13 (2009).

Newmeyer, D , et al., “Mitochondria: releasing power for life and unleashing the machineries of death”, Cell 112(4), 481-490 (2003).

Patent Cooperation Treaty , International Searching Authority, International Preliminary Report on Patentability for PCT/US2017/048482, 6 pages, report issued Feb. 26, 2019, opinion mailed Dec. 7, 2017.

Patent Cooperation Treaty , International Searching Authority, International Search Report for PCT/ US2017/048482, 4 pages, mailed Dec. 7, 2017.

PUBCHEM , “Substance Record: 7-(dimethylamino)-3H-phenothiazin-3-one”, Compound Summary for SID 224730291, https://pubchem.ncbi.nlm.nih.gov/substance/224730291, (Feb. 2, 2015).

Baraste, M , “Oxidative phosphorylation at the fin de siècle”, Science 283, 1488-1493 (1999).

Smith, A , “[13] Preparation, properties, and conditions for assay of mitochondria: Slaughterhouse material, small-scale”, Methods Enzymol 10, 81-86 (1967).

Smith, R , et al., “Mitochondrial pharmacology”, Trends in Pharmacological Sciences 33(6), 341-352 (2012).

Turrens, J , “Mitochondrial formation of reactive oxygen species”, J Physiol 552, 335-344 (2003).

Wainwright, M , et al., “Methylene blue—a therapeutic dye of all seasons?”, Journal of Chemotherapy 14(5), 431-443 (2002).

Wen, Y , et al., “Alternative Mitochondrial Electron Transfer as a Novel Strategy for Neuroprotection”, The Journal of Biological Chemistry 286(18), 16504-16515 (2011).

Wright, R , et al., “Methemoglobinemia: Etiology, Pharmacology, and Clinical Management”, Annals of Emergency Medicine 34(5), 646-656 (1999).

Yu, L , et al., “Synthesis and in vitro evaluation of α-synuclein ligands”, Bioorganic & Medicinal Chemistry 20(15), 4625-4634 (2012).

Zulian, G , et al., “Methylene Blue for Ifosfamide-Associated Encephalopathy”, The New England Journal of Medicine 332(18), 1239-1240 (1995).

* cited by examiner 1 2 3 4 5

THERAPEUTIC COMPOUNDS

CROSS-REFERENCE TO RELATED APPLICATIONS

This application is a continuation of U.S. patent application Ser. No. 16/924,763, filed Jul. 9, 2020, which is a divisional of U.S. patent application Ser. No. 16/327,284, filed Feb. 21, 2019, now U.S. Pat. No. 10,745,366, issued Aug. 18, 2020, which is a 35 U.S.C. § 371 application of International Application Serial No. PCT/US2017/048482, filed Aug. 24, 2017, which claims the benefit of U.S. Provisional Application Ser. No. 62/379,654, filed Aug. 25, 2016. The entire content of the applications referenced above are hereby incorporated by reference herein.

BACKGROUND OF THE INVENTION

Mitochondrial dysfunction and disruption of the electron transport chain (ETC) has been identified as an important factor in diseases ranging from neurodegenerative diseases including, Alzheimer's disease (AD), Parkinson's disease (PD) and Friedreich's ataxia (FRDA), to diseases of the cardiovascular system, cancer and diabetes (Armstrong, J. S. et al. *FASEB J.* 2010, 24, 2152; Markesbery, W. R. et al. *Brain Pathol.* 1999, 9, 133; Barnham, K. J.; Masters, C. L. et al. *Nat. Rev Drug Discovery.* 2004, 3, 205; Calabrese, V. et al. *J Neurol Sci.* 2005, 233, 145; and Lin, M. T. et al. *Nature* 2006, 443, 787). The broad impact of mitochondria in so many diseases makes them prime targets for therapeutics. As powerhouses in mammalian cells, mitochondria are responsible for the predominant mode of energy production via oxidative phosphorylation (OXPHOS) of glucose, which is performed by the four respiratory complexes (complexes I-IV) and the ATP synthase (complex V), all located in the inner mitochondrial membrane (Henze, K. et al. Nature 2003, 426, 127; Saraste, M. W. *Science* 1999, 283, 1488; Newmeyer, D. D. et al. S. *Cell* 2003, 112, 481; and Fiore, C. et al. *Biochimie* 1998, 80, 137). However, mitochondria are also the major sites for production of reactive oxygen species (ROS) (Turrens, J. F. *J. Physiol.* 2003, 552, 335; and Murphy, M. P. *Biochem. J.* 2009, 417, 1). The impaired oxidative phosphorylation function would lead to further production of ROS, which further overwhelms the endogenous antioxidant systems and exposing cellular macromolecules to oxidative damage (Mates, J. M. et al. *Clin Biochem.* 1999, 32, 595; and Gaetani, G. F. et al. *Blood* 1989, 73, 334). Giving the main role of mitochondrial dysfunction in the development of several metabolic disorders, extensive research has explored therapeutic strategies for preserving mitochondrial function and the treatment of mitochondrial and neurological diseases (Heller, G. et al. *Eur. J. Pharm. Biopharm.* 2012, 82, 1; Smith, R. A. et al. *Trends in Pharmacol. Sci.* 2012, 341; Frantz, M. C. et al. *Environ. Mol. Mutagen* 2010, 51, 462; Arce, P. M. et al. *ACS Med. Chem. Lett.* 2011, 2, 608; Atamna, H. et al. *FASEB. J.* 2008, 22, 703; and Wen, Y. et al. *J. Biol. Chem.* 2011, 286, 16504).

Methylene blue (MB), a member of the phenothiazine family, originally discovered as a synthetic cationic dye. MB has a long-standing, extensive history of medical uses for more than a century (Wainwright, M. et al. *J Chemother.* 2002,14,431). It is an FDA approved drug for methemoglobinemia and an antidote to ifosfamide-induced encephalopathy (Wright, R. et al. *Ann. Emerg. Med.* 1999, 34, 646; and Zulian, G. B. et al. *N. Engl J Med.* 1995, 332, 1239). MB was also the lead compound for successful pharmacotherapeutic derivatives such as the antimalarial agents such as quinacrine, and chloroquine (Green, R. Lancet 1932, 219, 826; and Loeb, R. F. et al. *J. Am. Med. Assoc.* 1946, 130, 1069).

MB has very unique redox property that exists in equilibrium between oxidized state in dark blue and colorless reduced state, making it both antioxidant and prooxidant under different conditions. MB with a mild redox potential, appears to readily cycle between the oxidized and reduced forms using specific mitochondrial and cytosolic redox centers. This property of MB has been reported to redirect and facilitate electron transfer across mitochondrial electron transfer complexes minimizing electron leakage, and inhibit superoxide production (mitochondria! electron-carrier bypass) (Wen, Y. et al. *J. Biol. Chem.* 2011, 286, 16504; and Wainwright, M. et al. *J Chemother.* 2002,14,431). Thus, MB might be able to act as an alternative electron transfer carrier that replaces the damaged mitochondrial respiratory chain.

Methylene blue has limitation in term of bioavailability and tolerability (at high doses). The substantial hydrophilicity of MB may restrict its permeability across the plasma membranes of mammalian cells, which would also limit its cellular uptake. It is for this reason TauRx switch to the reduced form of methylene blue (more hydrophobic) in their phase III clinical trials (Baddeley, T. C. et al. *J Pharmacol Exp Ther.* 2015, 352, 1; and Melis, V. et al. *Behav Pharmacol.* 2015, 26, 353). MB has a hormetic dose-response in which its beneficial effects are optimal in the lower to intermediate range (Bruchey A. K. et al. *Am J Pharm Toxicol* 2008, 3, 72). Previous study has shown the effect and interaction of exogenous short-chain $CoQ_{10}$ analogues on mitochondrial oxidative phosphorylation in isolated mitochondria and ROS metabolism in cultured cells. It was clearly showed that the antioxidant reactions of exogenous ubiquinones will predominantly occur within phospholipid bilayers, while the pro-oxidant reactions require an aqueous environment. It is apparent that increasing hydrophobicity limits the "bad" aqueous autoxidation of ubiquinols without diminishing its "good lipid phase antioxidant functions. This could provide explanation for the extreme hydrophobicity of endogenous $CoQ_{10}$. Therefore, the relative rates of these reactions can be fine-tuned by hydrophobicity, allowing a rational approach to the design of therapeutic mitochondria-targeted redox cyclers.

Methylene violet (MV) is a neutral phenothiazine dye. Hydrolysis of MB under strongly basic condition yields MV with improved hydrophobicity (Houghtaling, M. A. et al. *Photochem. Photobiol.* 2000, 71, 20). MV can be looked upon as a phenolic analogue of MB where a hydroxyl group substitutes one of the two dimethylamine moieties. Although MV is naturally obtained in the oxidized (quinone) form, it can be reduced by the mitochondrial redox centers generating the phenolic (quinol) form. The reduced form of MV can act as phenolic antioxidants similar to $CoQ_{10}$. Currently there is a need for new antioxidant compounds with reduced cytotoxicity and side effects (e.g. by decreasing the pro-oxidant effect).

SUMMARY OF THE INVENTION

The invention provides new antioxidant compounds with reduced cytotoxicity and side effects. Accordingly the invention provides a compound of formula I:

I

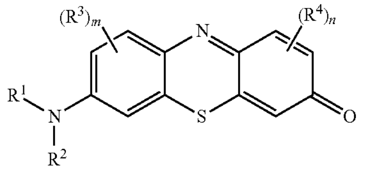

or a pharmaceutically acceptable salt thereof, wherein:

$R^1$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, oxo, —$NO_2$ and —CN;

$R^2$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, oxo, —$NO_2$ and —CN; or $R^1$ and $R^2$ taken together with the nitrogen to which they are attached form a 3-12 membered heterocycle that is optionally substituted with one or more groups independently selected from $C_{1-4}$ alkyl, $C_{1-4}$ haloalkyl, —F, —Cl, —Br, —I, —$OR^a$, —$SR^a$,oxo, —$NO_2$ and —CN;

each $R^3$ is independently selected from the group consisting of —F, —Cl, —Br, —I, —OH, ——$OR^a$, —$SR^a$,—CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, oxo, —$NO_2$ and —CN;

each $R^4$ is independently selected from the group consisting of —F, —Cl, —Br, —I, —$SR^a$, —$NR^aR^b$, —$NO_2$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, oxo, —$NO_2$ and —CN;

each $R^a$ is independently hydrogen or $C_{1-4}$ alkyl;

each $R^b$ is independently hydrogen or $C_{1-4}$ alkyl;

the subscript m is 0, 1, 2 or 3; and the subscript n is 0, 1, 2, or 3.

The invention also provides a pharmaceutical composition comprising a compound of formula I or a pharmaceutically acceptable salt thereof, and a pharmaceutically acceptable carrier.

The invention also provides a method for treating mitochondrial disease, neurodegenerative disease, cardiovascular disease, cancer or diabetes in an animal comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of mitochondrial disease, neurodegenerative disease, cardiovascular disease, cancer or diabetes.

The invention also provides the use of a compound of formula I or a pharmaceutically acceptable salt thereof to prepare a medicament for treating mitochondrial disease, neurodegenerative disease, cardiovascular disease, cancer or diabetes in an animal (e.g. a mammal such as a human).

The invention also provides processes and intermediates disclosed herein that are useful for preparing a compound of formula I or a salt thereof.

DETAILED DESCRIPTION

Figure 1:
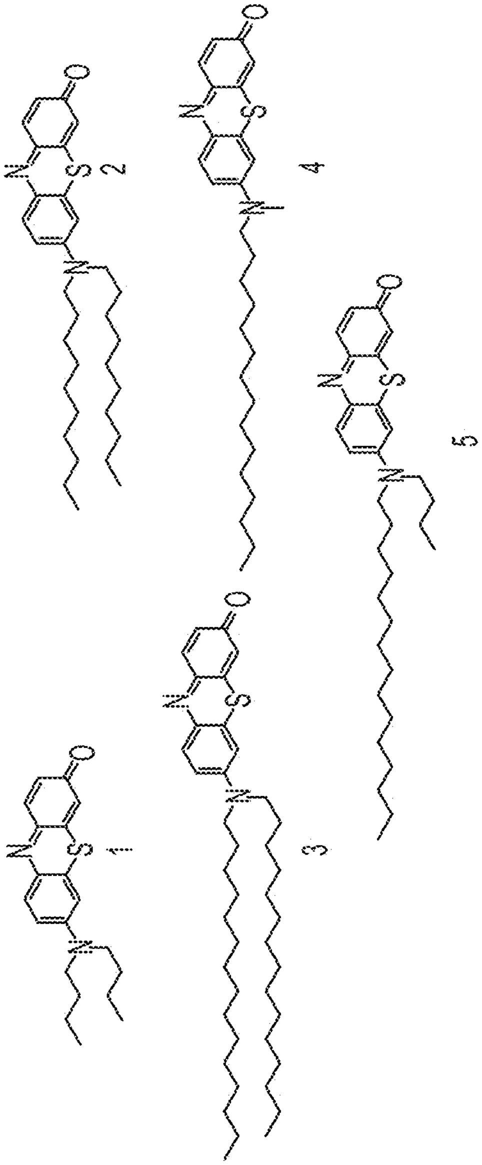
FIG. 1 illustrates the chemical structures of the representative compounds of formula I (compounds 1-5).

The term "alkyl", by itself or as part of another substituent, means, unless otherwise stated, a straight or branched chain hydrocarbon radical, having the number of carbon atoms designated (i.e., $C_1$-6 means one to six carbons). Non limiting examples of "alkyl" include methyl, ethyl, propyl, isopropyl, butyl, iso-butyl, sec-butyl, pentyl, 3-pentyl, hexyl and decyl.

The term "alkenyl" refers to an unsaturated alkyl radical having one or more double bonds. Non limiting examples of "alkenyl" include vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. Similarly, the term "alkynyl" refers to an unsaturated alkyl radical having one or more triple bonds.

The term "haloalkyl" means an alkyl that is optionally substituted with halo. Non limiting examples of "haloalkyl" include iodomethyl, bromomethyl, chloromethyl, fluoromethyl, trifluoromethyl, 2-chloroethyl, 2-fluoroethyl, 2,2,2-trifluoroethyl and pentafluoroethyl.

The term "heterocycle" refers to a saturated or partially unsaturated ring system radical having the overall having from 3-12 ring atoms that contain from one to five heteroatoms selected from N, O, and S. Unless otherwise stated, a "heterocycle" ring can be a monocyclic, a bicyclic, spirocyclic or a polycylic ring system. Non limiting examples of "heterocycle" rings include pyrrolidine, piperidine, N-methylpiperidine, imidazolidine, pyrazolidine, butyrolactam, valerolactam, imidazolidinone, hydantoin, dioxolane, phthalimide and piperidine.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

In one embodiment, the compound has the following formula Ia:

Ia

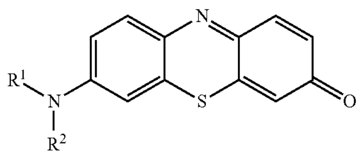

or a pharmaceutically acceptable salt thereof.

In one embodiment, $R^1$ is $C_{1-20}$ alkyl.

In one embodiment, $R^1$ is n-butyl, n-decyl or n-pentadecyl.

In one embodiment, $R^2$ is $C_{1-20}$ alkyl.

In one embodiment, $R^2$ is methyl, n-butyl, n-decyl or n-pentadecyl.

In one embodiment, m is 0 and n is 0.

In one embodiment, $R^1$ is $C_{12-20}$ alkyl, $C_{12-20}$ alkenyl or $C_{2-20}$ alkynyl, and wherein the $C_{2-20}$ alkyl, $C_{2-20}$ alkenyl and $C_{12-20}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl; and each $R^b$ is independently hydrogen or $C_{1-4}$ alkyl.

In one embodiment, the compound is selected from the group consisting of:

1

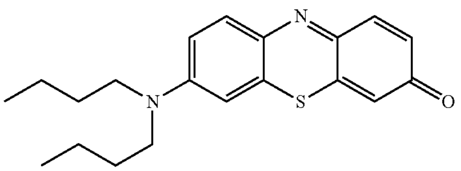 [SMILES: CCCCN(CCCC)c1ccc2nc3ccc(=O)cc-3sc2c1]

2

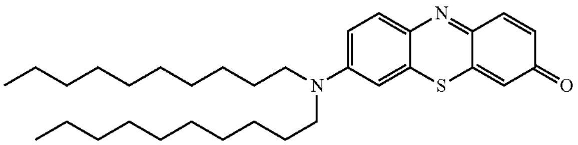

3

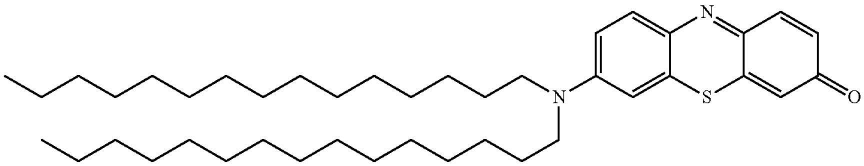

4

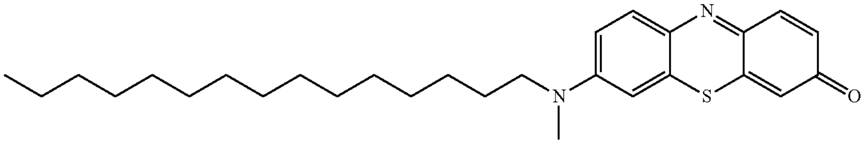

and

5

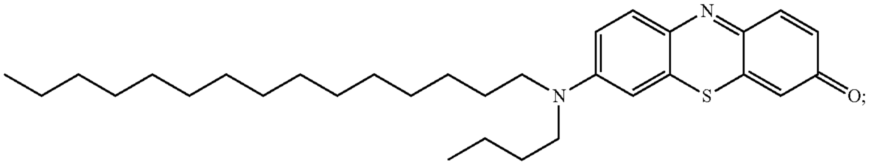

and pharmaceutically acceptable salts thereof.

In one embodiment, the neurodegenerative disease is Alzheimer's disease (AD), Parkinson's disease (PD) or Friedreich's ataxia (FRDA).

In one embodiment, the invention provides a method of preserving mitochondrial function in an animal comprising administering to the animal an effective amount of compound of formula (I) or a pharmaceutically acceptable salt thereof.

In one embodiment, the invention also provides a method of protecting cells from oxidative stress in an animal comprising administering to the animal an effective amount of compound of formula (I) or a pharmaceutically acceptable.

In one embodiment, the invention also provides a method of preserving mitochondrial membrane potential and/or augmenting ATP production in an animal comprising administering to the animal an effective amount of compound of formula (I) or a pharmaceutically acceptable salt thereof.

In another embodiment, the invention provides a method of preserving mitochondrial membrane potential and/or augmenting ATP production of a cell in vitro comprising contacting the cell with an effective amount of compound of formula (I) or a pharmaceutically acceptable salt thereof.

In one embodiment, the invention provides a compound of formula (I) or a pharmaceutically acceptable salt thereof for use in preserving mitochondrial function.

In one embodiment the invention provides a compound of formula (I) or a pharmaceutically acceptable salt thereof for use in protecting cells from oxidative stress.

In one embodiment, the invention provides a compound of formula (I) or a pharmaceutically acceptable salt thereof for use in preserving mitochondrial membrane potential and/or augmenting ATP production.

In one embodiment, the invention provides the use of a compound of formula (I) or a pharmaceutically acceptable salt thereof for the manufacture of a medicament for preserving mitochondrial function.

In one embodiment, the invention provides the use of a compound of formula (I) or a pharmaceutically acceptable salt thereof for the manufacture of a medicament for protecting cells from oxidative stress.

In one embodiment, the invention provides the use of a compound of formula (I) or a pharmaceutically acceptable salt thereof for the manufacture of a medicament for preserving mitochondrial membrane potential and/or augmenting ATP production.

Processes for preparing compounds of formula I are provided as further embodiments of the invention and are illustrated by the following procedures in which the meanings of the generic radicals are as given above unless otherwise qualified.

A compound of formula I can be prepared by converting a corresponding compound of formula II to provide the compound of formula I or a pharmaceutically acceptable salt thereof:

II

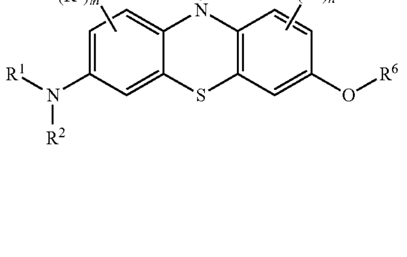

wherein:

$R^1$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN;

$R^2$ is $C_{1-20}$ alkyl, $C_{2-20}$ alkenyl or $C_{2-20}$ alkynyl, and wherein the $C_{1-20}$ alkyl, $C_{2-20}$ and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN; or $R^1$ and $R^2$ taken together with the nitrogen to which they are attached form a 3-12 membered heterocycle that is optionally substituted with one or more groups independently selected from $C_{1-4}$ alkyl, $C_{1-4}$ haloalkyl, —F, —Cl, —Br, —I, —$OR^a$, —$SR^a$, oxo, —$NO_2$ and —CN;

each $R^3$ is independently selected from the group consisting of —F, —Cl, —Br, —I, —OH, —$OR^a$, —$SR^a$,—CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^4$ is independently selected from the group consisting of —F, —Cl, —Br, —I, —$SR^a$, —$NR^1R^b$, —$NO_2$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

$R^5$ is $C_{1-10}$ alkyl that is optionally substituted with one or more groups independently selected from —F, —Cl, —Br, —I, —$OR^a$, —$SR^a$, —$NR^aR^b$, oxo, —$NO_2$ and —CN;

$R^6$ is hydrogen or $C_{1-6}$ alkyl that is optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl;

each $R^b$ is independently hydrogen or $C_{1-4}$ alkyl;

the subscript m is 0, 1, 2 or 3; and the subscript n is 0, 1, 2, or 3;

or a salt thereof.

An important intermediate to provide a compound of formula II is a compound of formula III. A compound of formula III can be prepared by converting a corresponding compound of formula IV to provide the compound of formula III:

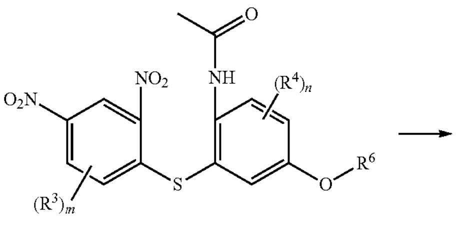

IV

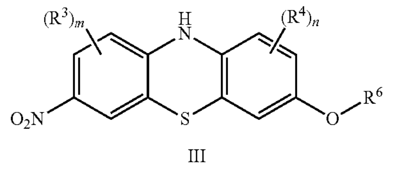

III wherein:

each $R^3$ is independently selected from the group consisting of —F, —Cl, —Br, —I, —OH, —$OR^a$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^4$ is independently selected from the group consisting of —F, —Cl, —Br, —I, —$OR^a$, —$SR^a$, —$NR^aR^b$, —$NO_2$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

$R^6$ is hydrogen or $C_1$-6 alkyl that is optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl;

each $R^b$ is independently hydrogen or $C_{1-4}$ alkyl;

the subscript m is 0, 1, 2 or 3; and the subscript n is 0, 1, 2, or 3;

or a salt thereof.

Compounds of formula (I) may be prepared by the process illustrated in Schemes 1 and 2. Representative compounds of formula (I) are compounds 1-5 (FIG. 1).

Scheme 1. Synthesis of compounds 1, 2, and 3.

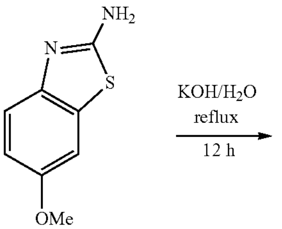

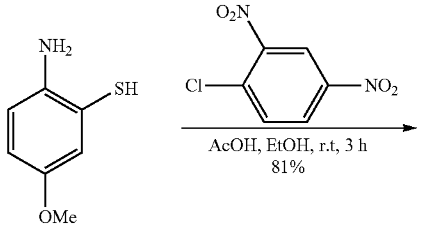

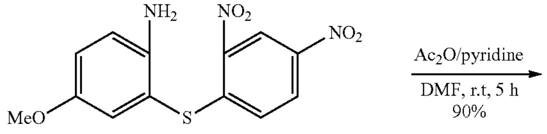

7

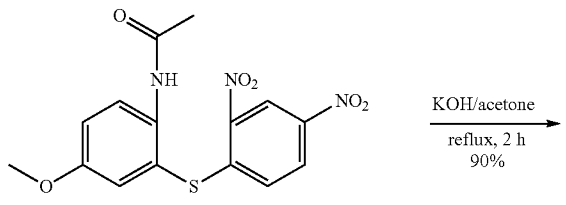

8

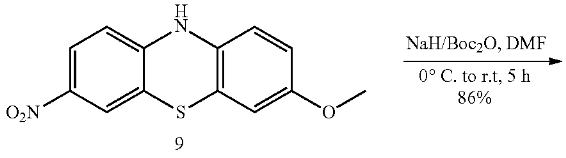

9

-continued

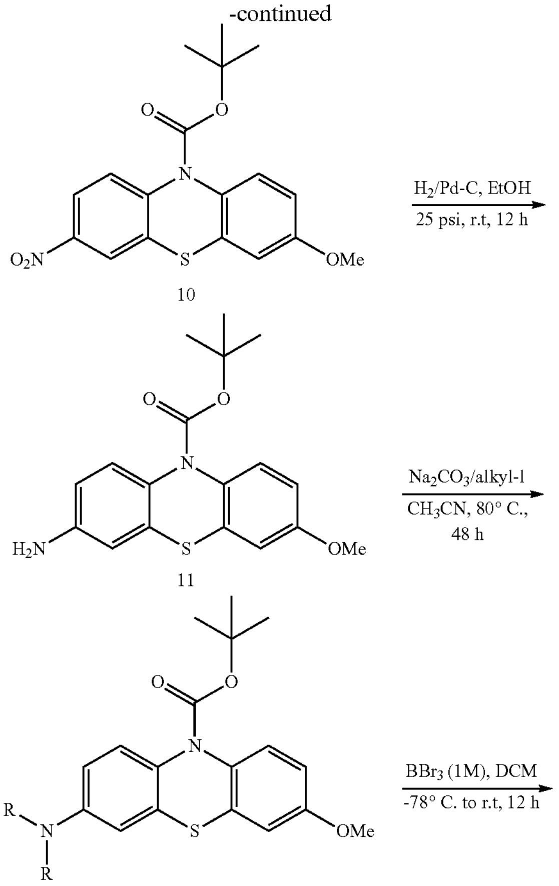

61% R = n-butyl 12
5% R = n-decyl 13
— R = n-pentadecyl 14

-continued

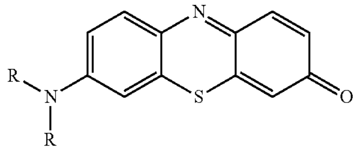

47% R = n-butyl 1
38% R = n-decyl 2
44% R = n-pentadecyl 3

Hydrolysis of 2-amino-6-methoxybenzothiazole under strongly basic conditions afforded 2-amino-5-methoxybenzothiol which was coupled with 2, 4-dinitrochlorobenzene to obtain substituted diphenylsulfide intermediate 7 in 81% yield (Yu, L. et al. *Bioorg. Med. Chem.* 2012, 20, 4625). Compound 7 was treated with acetic anhydride in presence of triethylamine in order to activate the amine as acetamide intermediate 8 in 90% yield. Smiles rearrangement of 8 under mild basic conditions afforded the substituted phenothiazine intermediate 9 in 90% yield (Yu, L. et al. *Bioorg. Med. Chem.* 2012, 20, 4625). Compound 9 was then treated with 60% NaH followed by di-tent-butyl dicarbonate to obtain 10 in 86% yield. Hydrogenolysis of 10 in presence of Pd-C afforded 11, which was alkylated with different alkyl iodides in the presence of $Na_2CO_3$ as base to obtain 12-14 in varying yields. In order to remove the O-methyl group to afford the free hydroxyl group at position 7, compounds 12-14 were treated with 1 M $BBr_3$ in $CH_2Cl_2$. The HBr, formed in situ, effected removal of the Boc group at the same time generating the desired compounds 1-3 in yields varying from 38% to 50%.

Scheme 2. Synthesis of compounds 4 and 5.

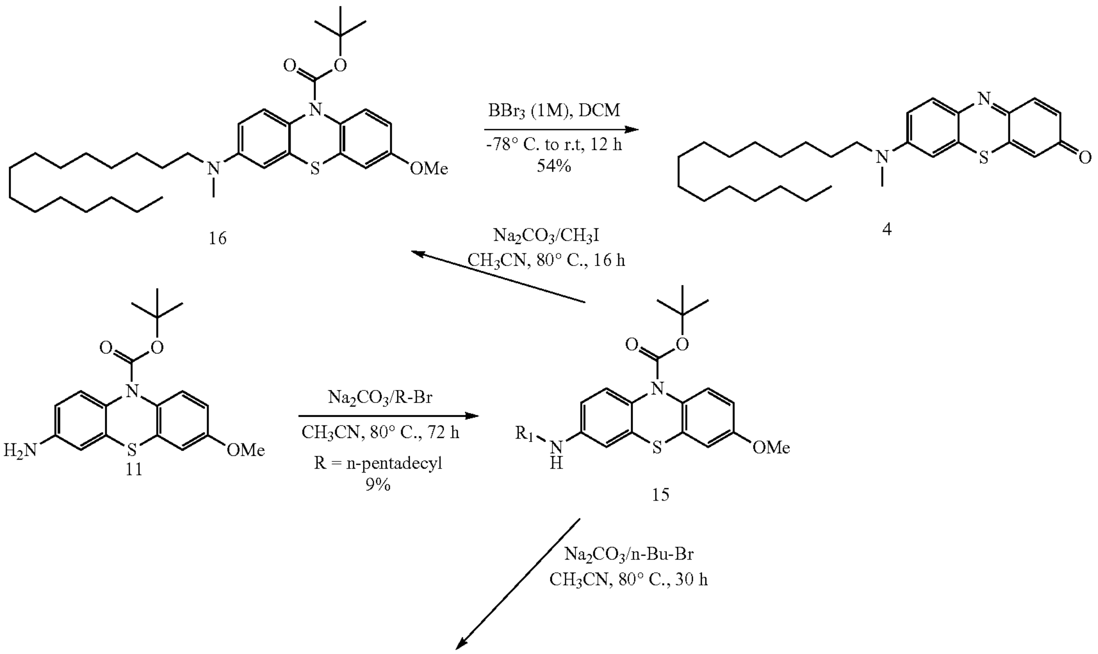

-continued

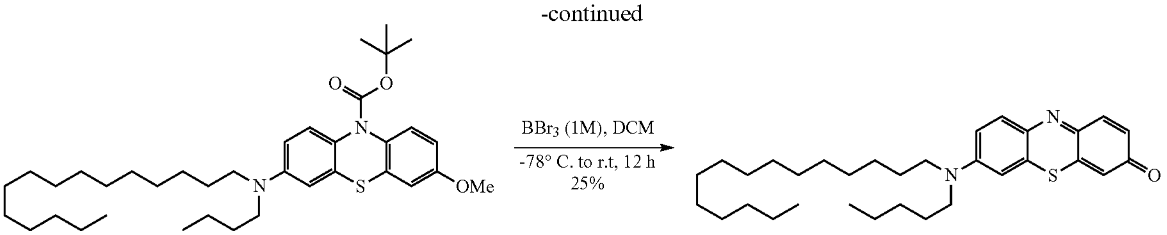

17 5

In order to synthesize compounds 4 and 5 compound 11 was first alkylated using 1-bromopentadecane. The mono-alkylated product 15 was purified on a silica gel column and was subsequently alkylated using either methyl iodide or 1-bromobutane to afford 16 and 17, respectively. Compounds 16 and 17 were subsequently treated with 1 M $BBr_3$ to afford 4 and 5, respectively.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula Ito the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

Example 1

Synthesis of 7-(N,N-Dibutylamino)-3H-phenothiazin-3-one (1)

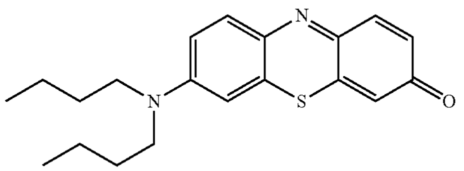

Step 1. Synthesis of 2-(2,4-Dinitrophenyl)thio)-5-methoxyaniline (7)

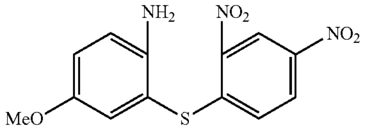 [SMILES: COc1ccc(N)c(Sc2ccc([N+](=O)[O-])cc2[N+](=O)[O-])c1]

A sample of 2.00 g (11.1 mmol) of 2-amino-6-methoxybenzothiazole was suspended in 40 mL of water and 9.30 g (167 mmol) of solid KOH was added. The suspension was heated to reflux for 12 h. The reaction mixture was cooled to room temperature and added dropwise to a solution of 2.25 g (11.1 mmol) of 2, 4-dinitrochlorobenzene in a mixture of ethanol (30 mL)-AcOH (20 mL) in ice-water bath. The reaction mixture was stirred at room temperature for an additional 3 h. The precipitate was filtered, washed with water-ethanol (1:1, v/v) and dried to afford 7 as an orange solid: yield 2.90 g (81%); silica gel TLC $R_f$ 0.7 (3:7 ethyl acetate-hexanes); $^1$H NMR ($CD_3COCD_3$) δ 3.76 (s, 3H), 6.85 (d, 1H, J=8.8 Hz), 6.97 (d, 1H, J=2.8 Hz), 7.00-7.06 (m, 2H), 8.18 (dd, 1H, J=9.2 Hz, J=2.6 Hz) and 9.12 (d, 1H, J=2.4 Hz); 13C NMR (DMSO-$d_6$) δ 55.9, 111.0, 117.5, 120.4, 120.6, 121.6, 127.1, 128.6, 143.3, 144.4, 144.6, 145.8 and 153.0; mass spectrum (APCI), m/z 322.0499 $(M+H)^+$ ($C_{13}H_{12}N_3O_5S$ requires m/z 322.0498).

Step 2. Synthesis of N-(2-((2,4-Dinitrophenyl)thio)-5-methoxyphenyl)acetamide (8)

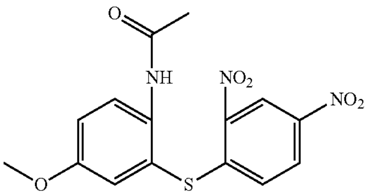 [SMILES: COc1ccc(NC(C)=O)c(Sc2ccc([N+](=O)[O-])cc2[N+](=O)[O-])c1]

To a solution of 2.90 g (9.03 mmol) of 7 in 10 mL of anhydrous DMF was added 3.66 mL (2.74 g, 27.1 mmol) of anhydrous triethylamine followed by 4.30 mL (4.64 g, 45.5 mmol) of acetic anhydride. The reaction mixture was stirred for 12 h at room temperature under an argon atmosphere and was quenched by pouring into ice-cold water. The aqueous layer was extracted with four 25-mL portions of ethyl acetate. The combined organic layer was dried over anhydrous $MgSO_4$, filtered and concentrated under diminished pressure. The residue was purified on a silica gel column (8×4 cm). Elution with 3:7 ethyl acetate-hexanes afforded 8 as a bright yellow solid: yield 2.95 g (90%); silica gel TLC $R_f$ 0.57 (3:7 ethyl acetate-hexanes); $^1$H NMR (DMSO-$d_6$) δ 1.86 (s, 3H), 3.77 (s, 3H), 6.99 (d, 1H, J=8.8 Hz), 7.18 (dd, 1H, J=8.8 Hz, J=2.4 Hz), 7.23 (d, 1H, J=2.8 Hz), 7.66 (d, 1H, J=8.8 Hz), 8.32 (dd, 1H, J=9.0 Hz, J=2.6 Hz), 8.88 (d, 1H, J=2.4 Hz) and 9.43 (br s, 1H); $^{13}$C NMR (DMSO-$d_6$) δ 22.8, 55.6, 117.7, 120.5, 121.0, 123.8, 127.5, 128.1, 129.2, 133.7, 144.05, 144.07, 145.6, 157.2 and 168.7; mass spectrum (APCI), m/z 364.0609 $(M+H)^+$ ($C_{15}H_{14}N_3O_6S$ requires m/z 364.0603).

Step 3. Synthesis of 3-Methoxy-7-nitro-10H-phenothiazine (9)

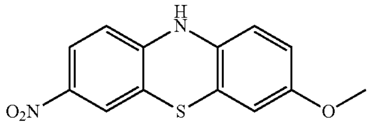 [SMILES: COc1ccc2c(c1)Sc1cc([N+](=O)[O-])ccc1N2]

To a stirred solution of 2.95 g (8.13 mmol) of 8 in 20 mL of acetone, at reflux, was added in portions 0.91 g (16.2 mmol) of KOH in 10 mL of ethanol. The reaction mixture was kept at reflux for an additional 3 h and poured into ice-cold water. The aqueous layer was extracted with four 25-mL portions of ethyl acetate. The combined organic layer was dried over anhydrous $MgSO_4$, filtered and concentrated under diminished pressure. The residue was purified on a silica gel column (8×2 cm). Elution with 1:1 ethyl acetate-hexanes gave 9 as a violet solid: yield 2.00 g (90%); silica gel TLC $R_f$ 0.43 (3:7 ethyl acetate-hexanes); $^1$H NMR ($CD_3COCD_3$) δ 3.70 (s, 3H), 6.57-6.70 (m, 4H), 7.73 (d, 1H, J=2.4 Hz), 7.81-7.84 (m, 1H) and 8.47 (br s, 1H); $^{13}$C NMR ($CD_3COCD_3$) δ 55.0, 111.7, 113.0, 113.3, 116.1, 117.0, 117.2, 121.6, 124.2, 132.4, 141.5, 148.3 and 156.6; mass spectrum (APCI), m/z 275.0488 $(M+H)^+$ ($C_{13}H_{11}N_2O_3S$ requires m/z 275.0490).

Step 4. Synthesis of tent-Butyl 3-Methoxy-7-nitro-10H-phenothiazin-10-carboxylate (10)

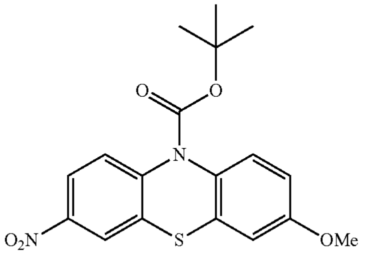 [SMILES: COc1ccc2c(c1)Sc1cc([N+](=O)[O-])ccc1N2C(=O)OC(C)(C)C]

To a solution of 1.42 g (5.18 mmol) of 9 in 20 mL of anhydrous DMF at 0° C. was added 0.55 g (13.7 mmol) of 60% NaH. The reaction mixture was stirred at 0° C. for another 15 min and 2.40 g (11.0 mmol) of di-tent-butyl dicarbonate was added. The reaction mixture was stirred at room temperature for 4 h under an arogon atmosphere, and was quenched with 30 mL of water. The aqueous layer was extracted with three 20-mL portions of ethyl acetate. The combined organic layer was washed with 20 mL of brine, dried over anhydrous $MgSO_4$ and concentrated under diminished pressure. The residue was purified on a silica gel column (8×4 cm). Elution with 3:7 ethyl acetate-hexanes afforded 10 as a bright yellow solid: yield 1.66 g (86%); silica gel TLC $R_f$ 0.54 (3:7 ethyl acetate-hexanes); $^1$H NMR ($CD_3COCD_3$) δ 1.54 (s, 9H), 3.86 (s, 3H), 6.97 (dd, 1H, J=9.2 Hz, J=2.8 Hz), 7.01 (d, 1H, J=2.8 Hz), 7.47 (d, 1H, J=9.2 Hz), 7.84 (d, 1H, J=8.8 Hz), 8.20 (dd, 1H, J=9.0 Hz, J=2.6 Hz) and 8.24 (d, 1H, J=2.4 Hz); $^{13}$C NMR ($CD_3COCD_3$) δ 29.2, 57.1, 84.3, 113.3, 115.6, 123.7, 124.1, 129.8, 130.0, 132.3, 133.1, 135.3, 146.9, 147.1, 153.2 and 159.9; mass spectrum (APCI), m/z 374.0932 $(M+H)^+$ ($C_{18}H_{19}N_2O_5S$ requires m/z 374.0936).

Step 5. Synthesis of tent-Butyl 3-Amino-7-methoxy-10H-phenothiazin-10-carboxylate (11)

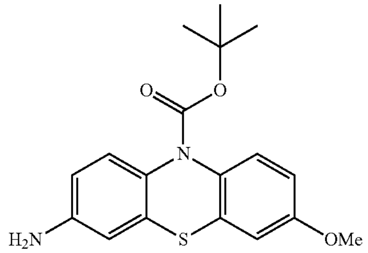

To a suspension of 0.42 g (1.12 mmol) of 10 in 10 mL of ethanol was added 10 mg of 10% Pd on carbon. The reaction mixture was stirred at room temperature under a hydrogen atmosphere (25 psi) overnight. The reaction mixture was filtered through a Celite pad and was concentrated under diminished pressure. The crude product (11) was used for the next reaction without further purification.

Step 6. Synthesis of tent-Butyl 3-(N,N-Dibutylamino)-7-methoxy-10H-phenothiazin-10-carboxylate

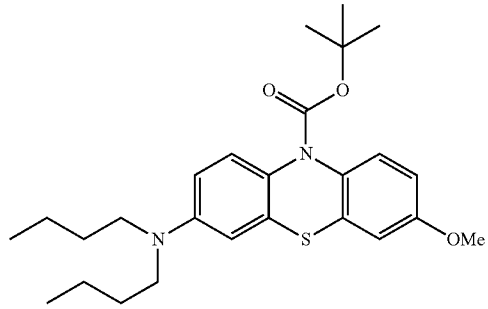 [SMILES: CCCCN(CCCC)c1ccc2c(c1)Sc1cc(OC)ccc1N2C(=O)OC(C)(C)C]

To a solution of crude 11 in 3 mL of acetonitrile was added 1.40 g (12.8 mmol) of $Na_2CO_3$ followed by 0.94 g (5.12 mmol) of 1-iodobutane. The reaction mixture was sealed under nitrogen atmosphere and stirred at 80° C. overnight. The reaction mixture was cooled to room temperature and filtered. The filtrate was concentrated under diminished pressure and purified on a silica gel column (10×2 cm). Elution with 1:9 ethyl acetate-hexanes gave compound 12 as a pale yellow solid: yield 0.31 g (61%); silica gel TLC $R_f$ 0.43 (1:9 ethyl acetate-hexanes); $^1$H NMR ($CDCl_3$) δ 0.95 (t, 6H, J=7.4 Hz), 1.32-1.37 (m, 4H), 1.49 (s, 9H), 1.51-1.57 (m, 4H), 3.23 (t, 4H, J=7.6 Hz), 3.78 (s, 3H), 6.52-6.55 (m, 2H), 6.78 (dd, 1H, J=8.8 Hz, J=2.8 Hz), 6.86 (d, 1H, J=2.8 Hz), 7.31 (d, 1H, J=8.4 Hz) and 7.39 (d, 1H, J=8.8 Hz); $^{13}$C NMR ($CDCl_3$) δ 13.9, 20.2, 28.1, 29.2, 50.8, 55.5, 81.2, 109.1, 110.2, 111.5, 112.6, 126.8, 127.2, 127.5, 132.3, 132.5, 133.2, 146.2, 153.2 and 157.0; mass spectrum (APCI), m/z 457.2530 $(M+H)^+$ ($C_{26}H_{37}N_2O_3S$ requires m/z 457.2525).

Step 7. Synthesis of 7-(N,N-Dibutylamino)-3H-phenothiazin-3-one (1)

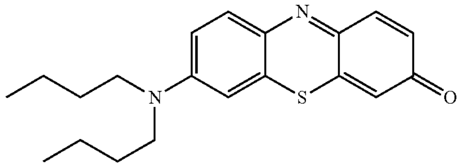 [SMILES: CCCCN(CCCC)c1ccc2nc3ccc(=O)cc-3sc2c1]

To a solution of 86.0 mg (0.19 mmol) of 12 in 2 mL of anhydrous $CH_2Cl_2$ was added dropwise 0.76 mL (0.76 mmol) of 1 M $BBr_3$ in $CH_2Cl_2$ at −78° C. The reaction mixture was stirred overnight at room temperature under an argon atmosphere and was quenched with 10 mL of water. The aqueous layer was extracted with two 10-mL portions of ethyl acetate. The combined organic layer was washed with 10 mL of brine, dried over anhydrous $MgSO_4$ and concentrated under diminished pressure. The residue was purified on a silica gel column (7×2 cm). Elution with 1:1 ethyl acetate-hexanes afforded 1 as a violet solid: yield 30 mg (47%); silica gel TLC $R_f$ 0.42 (1:1 ethyl acetate-hexanes); $^1$H NMR ($CDCl_3$) δ 0.95 (t, 6H, J=7.4 Hz), 1.26-1.37 (m, 4H), 1.51-1.57 (m, 4H), 3.23 (m, 4H), 6.52-6.55 (m, 2H), 6.76-6.87 (m, 2H), 7.31 (d, 1H, J=8.8 Hz) and 7.38 (d, 1H, J=8.8 Hz); mass spectrum (APCI), m/z 341.1690 $(M+H)^+$ ($C_{20}H_{25}N_2OS$ requires m/z 341.1688).

Example 2

Synthesis of 7-(N,N-Didecylamino)-3H-phenothiazin-3-one (2)

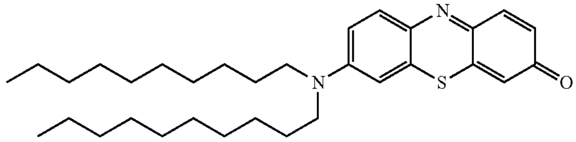 [SMILES: CCCCCCCCCCN(CCCCCCCCCC)c1ccc2nc3ccc(=O)cc-3sc2c1]

Step 1. Synthesis of tert-Butyl 3-(N,N-Didecylamino)-7-methoxy-10H-phenothiazin-10-carboxylate (13)

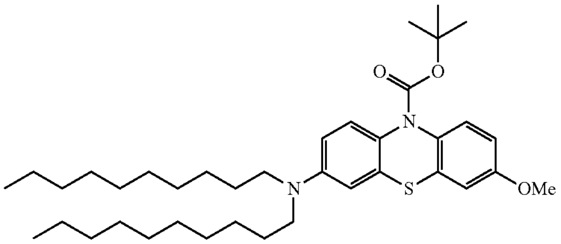 [SMILES: CCCCCCCCCCN(CCCCCCCCCC)c1ccc2c(c1)Sc1cc(OC)ccc1N2C(=O)OC(C)(C)C]

0.74 g (2.90 mmol) of 1-iododecane in 2 mL of acetonitrile was added into a mixture of 0.40 g (~1.16 mmol) of crude 11 in 2 mL of acetonitrile and 1.23 g (11.6 mmol) of $Na_2CO_3$. The reaction mixture was sealed under nitrogen atmosphere and stirred at 80° C. for 48 h. The reaction mixture was cooled to room temperature and filtered. The filtrate was concentrated under diminished pressure and purified on a silica gel column (8×2 cm). Elution with 1:19 ethyl acetate-hexanes gave compound 13 as a pale yellow solid: yield 30 mg (5%); silica gel TLC $R_f$ 0.41 (1:19 ethyl acetate-hexanes) $^1$H NMR ($CDCl_3$) δ 0.81 (t, 6H, J=6.8 Hz), 1.19 (m, 28H), 1.22 (s, 9H), 1.40-1.46 (m, 4H), 3.13 (t, 4H, J=7.6 Hz), 3.69 (s, 3H), 6.42-6.44 (m, 2H), 6.90 (dd, 1H, J=8.6 Hz, J=2.6 Hz), 6.70 (d, 1H, J=2.8 Hz), 7.21 (d, 1H, J=8.4 Hz) and 7.30 (d, 1H, J=8.8 Hz); $^{13}$C NMR ($CDCl_3$) δ 14.1, 22.7, 27.1, 28.2, 29.3, 29.5, 29.6, 31.9, 51.2, 55.5, 81.2, 109.1, 110.2, 111.6, 112.6, 126.8, 127.3, 127.6, 132.4, 132.6, 133.2, 146.3, 153.3 and 157.1; mass spectrum (APCI), m/z 625.4390 $(M+H)^+$ ($C_{38}H_{61}N_2O_3S$ requires m/z 625.4403).

Step 2. Synthesis of 7-(N,N-Didecylamino)-3H-phenothiazin-3-one (2)

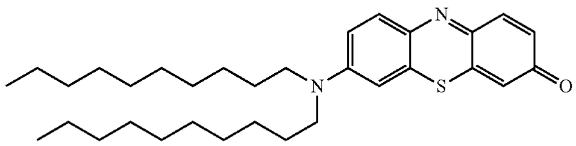 [SMILES: CCCCCCCCCCN(CCCCCCCCCC)c1ccc2nc3ccc(=O)cc-3sc2c1]

0.20 mL (0.20 mmol) of 1 M $BBr_3$ in $CH_2Cl_2$ was added dropwise into a solution of 30.0 mg (0.05 mmol) of compound 13 in 4 mL of $CH_2Cl_2$ at −78° C. The reaction mixture was stirred overnight at ambient temperature and was quenched with 10 mL of water. The product was extracted with two 10-mL portions of ethyl acetate. The violet organic layer was washed with 20 mL of brine, dried over anhydrous $Na_2SO_4$ and concentrated under reduced pressure.

The resulting violet solid was purified on a silica gel column (7×2 cm). Elution with 1:2 ethyl acetate-hexanes afforded 2 as a violet solid: yield 9 mg (38%); silica gel TLC $R_f$ 0.50 (1:2 ethyl acetate-hexanes); 1H NMR ($CDCl_3$) δ 0.87 (t, 6H, J=6.8 Hz), 1.24-1.34 (m, 28H), 1.63 (br s, 4H), 3.36 (t, 4H, J=7.8 Hz), 6.51 (d, 1H, J=2.8 Hz), 6.66 (d, 1H, J=2.0 Hz), 6.75-6.82 (m, 2H), 7.53 (d, 1H, J=9.6 Hz) and 7.46 (d, 1H, J=9.2 Hz); $^{13}$C NMR ($CDCl_3$) δ14.1, 22.6, 27.0, 27.3, 29.3, 29.4, 29.50, 29.54, 29.7, 31.8, 51.4, 104.7, 113.2, 118.4, 128.6, 130.9, 132.1, 134.8, 135.9, 139.4, 139.6, 149.8 and 182.1; mass spectrum (APCI), m/z 509.3553 $(M+H)^+$ ($C_{32}H_{49}N_2OS$ requires m/z 509.3566).

Example 3

Synthesis of 7-(N,N-Dipentadecylamino)-3H-phenothiazin-3-one (3)

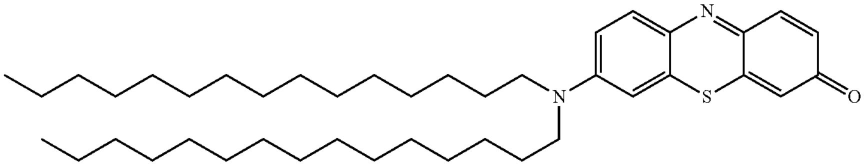 [SMILES: CCCCCCCCCCCCCCCN(CCCCCCCCCCCCCCC)c1ccc2nc3ccc(=O)cc-3sc2c1]

Step 1. Synthesis of tent-Butyl 3-(N,N-Dipentadecylamino)-7-methoxy-10H-phenothiazin-10-carboxylate (14).

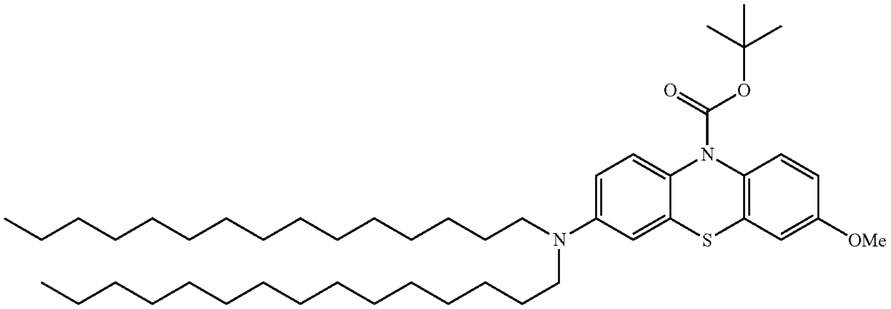 [SMILES: CCCCCCCCCCCCCCCN(CCCCCCCCCCCCCCC)c1ccc2c(c1)Sc1cc(OC)ccc1N2C(=O)OC(C)(C)C]

0.98 g (2.90 mmol) of 1-iodopentadecane in 2 mL of acetonitrile was added into a mixture of 0.40 g (~1.16 mmol) of crude 11 in 2 mL of acetonitrile and 1.23 g (11.6 mmol) of $Na_2CO_3$. The reaction mixture was sealed under nitrogen atmosphere and stirred at 80° C. for ~48 h. The reaction mixture was cooled to room temperature and filtered. The filtrate was concentrated under diminished pressure and purified on a silica gel column to remove the unreacted starting material (8×2 cm). Elution with 1:19 ethyl acetate-hexanes gave a mixture of mono and dialkylated product as a yellow oil.

Step 2. Synthesis of 7-(N,N-Dipentadecylamino)-3H-phenothiazin-3-one (3)

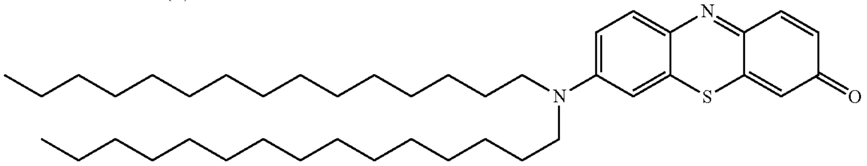

0.28 mL (0.28 mmol) of 1 M $BBr_3$ in $CH_2Cl_2$ was added dropwise into the solution of 50.0 mg of crude compound 14 in 2 mL of $CH_2Cl_2$ at −78° C. The reaction mixture was stirred overnight at ambient temperature and was quenched with 10 mL of water. The product was extracted with two 10-mL portions of ethyl acetate. The combined organic layer was washed with 20 mL of brine, dried over anhydrous $Na_2SO_4$ and concentrated under reduced pressure. The resulting violet solid was purified on a silica gel column. Elution with 1:4 ethyl acetate-hexanes afforded 3 as a violet solid: yield 20 mg (44%); silica gel TLC $R_f$ 0.50 (1:4 ethyl acetate-hexanes); 1H NMR ($CDCl_3$) δ 0.88 (t, 6H, J=6.8 Hz), 1.26-1.35 (m, 48H), 1.62-1.64 (m, 4H), 3.37 (t, 4H, J=7.6 Hz), 6.53 (d, 1H, J=2.8 Hz), 6.67 (d, 1H, J=2.0 Hz), 6.76-6.84 (m, 2H), 7.55 (d, 1H, J=9.6 Hz) and 7.66 (d, 1H, J=9.2 Hz); $^{13}C$ NMR ($CDCl_3$) δ 30 14.3, 22.8, 27.1, 27.5, 29.50, 29.53, 29.6, 29.7, 29.77, 29.79, 29.81, 29.83, 32.1, 51.5, 104.8, 113.3, 118.7, 128.7, 131.0, 132.4, 134.9, 136.0, 139.6, 140.0, 150.0 and 182.4; mass spectrum (APCI), m/z 648.5144 $(M+H)^+$ ($C_{42}H_{69}N_2OS$ requires m/z 649.5131).

Example 4

Synthesis of 7-(N-Methyl-N-pentadecylamino)-3H-phenothiazin-3-one (4)

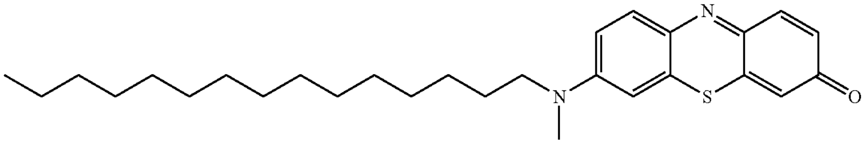 [SMILES: CCCCCCCCCCCCCCCN(C)c1ccc2nc3ccc(=O)cc-3sc2c1]

Step 1. Synthesis of tert-Butyl 3-(N-Pentadecylamino)-7-methoxy-10H-phenothiazin-10-carboxylate (15).

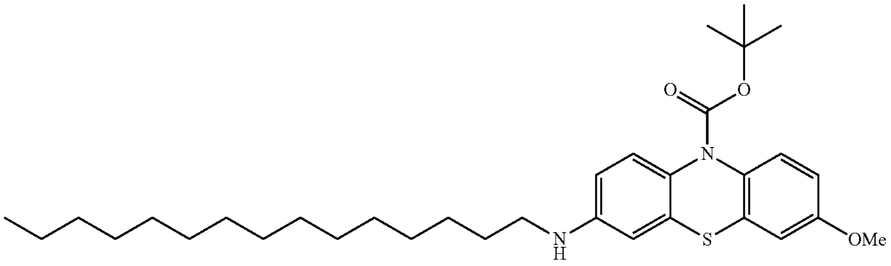 [SMILES: CCCCCCCCCCCCCCCNc1ccc2c(c1)Sc1cc(OC)ccc1N2C(=O)OC(C)(C)C]

2.11 g (7.25 mmol) of 1-bromopentadecane in 3 mL of acetonitrile was added into a mixture of 0.50 g (~1.45 mmol) of crude compound 11 in 2 mL of acetonitrile and 1.55 g (14.6 mmol) of $Na_2CO_3$. The reaction mixture was sealed under nitrogen atmosphere and stirred at 80° C. for ~3 days. The reaction mixture was cooled to room temperature and filtered. The filtrate was concentrated under diminished pressure and purified on a silica gel column. Elution with 1:9 ethyl acetate-hexanes gave compound 15 as a pale yellow solid: yield 0.14 g (9%); silica gel TLC $R_f$ 0.31 (1:9 ethyl acetate-hexanes); $^1H$ NMR ($CDCl_3$) δ 0.87 (t, 3H, J=6.6 Hz), 1.25 (br s, 24H), 1.45 (s, 9H), 1.52-1.57 (m, 2H), 3.04 (t, 2H, J=7.2 Hz), 3.76 (s, 3H), 6.45 (dd, 1H, J=8.6 Hz, J=2.6 Hz), 6.50 (d, 1H, J=2.8 Hz), 6.76 (dd, 1H, J=8.8 Hz, J=2.8 Hz), 6.83 (d, 1H, J=2.8 Hz), 7.24 (d, 1H, J=8.4 Hz) and 7.36 (d, 1H, J=8.8 Hz); $^{13}C$ NMR ($CDCl_3$) δ 14.2, 22.8, 27.2, 28.20, 28.27, 28.31, 28.4, 29.46, 29.5, 29.69, 29.70, 29.75, 29.8, 32.0, 44.2, 55.7, 81.4, 109.8, 111.65, 111.7, 112.8, 127.6, 127.8, 128.7, 132.5, 132.7, 133.3, 146.7, 153.3 and 157.3; mass spectrum (APCI), m/z 555.3629 $(M+H)^+$ ($C_{33}H_{51}N_2O_3S$ requires m/z 555.3620).

Step 2. Synthesis of tert-Butyl 3-(N-Methyl-N-pentadecylamino)-7-methoxy-10H-phenothiazin-10-carboxylate (16).

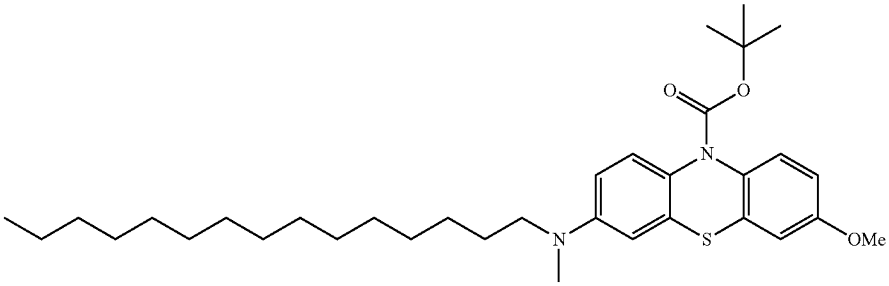 [SMILES: CCCCCCCCCCCCCCCN(C)c1ccc2c(c1)Sc1cc(OC)ccc1N2C(=O)OC(C)(C)C]

7.00 μL (16.0 mg, 0.11 mmol) of iodomethane was added into a mixture of 53.0 mg (0.10 mmol) of compound 15 in 2 mL of acetonitrile and 16.0 mg (0.15 mmol) of $Na_2CO_3$. The reaction mixture was sealed under nitrogen atmosphere and stirred at 80° C. for ~16 h.

The reaction mixture was cooled to room temperature and filtered. The filtrate was concentrated under diminished pressure. The crude was used to the next step without further purification.

Step 3. Synthesis of 7-(N-Methyl-N-pentadecylamino)-3H-phenothiazin-3-one (4)

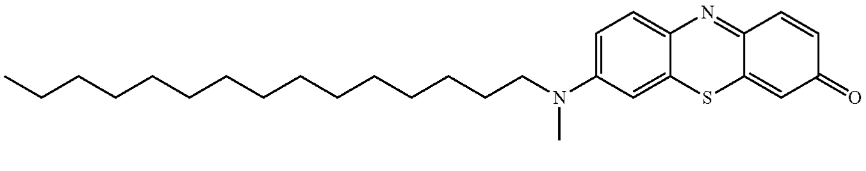 [SMILES: CCCCCCCCCCCCCCCN(C)c1ccc2nc3ccc(=O)cc-3sc2c1]

0.27 mL (0.27 mmol) of 1 M $BBr_3$ in $CH_2Cl_2$ was added dropwise into the solution of 50.0 mg of crude 16 in 2 mL of $CH_2Cl_2$ at −78° C. The reaction mixture was stirred overnight at room temperature and was quenched with 10 mL of water. The product was extracted with two 10-mL portions of ethyl acetate. The combined organic layer was washed with 20 mL of brine, dried over anhydrous $Na_2SO_4$ and concentrated under reduced pressure. The resulting violet solid was purified on a silica gel column (7×2 cm). Elution with 3:7 ethyl acetate-hexanes afforded 5 as a violet solid: yield 22 mg (54%); silica gel TLC $R_f$ 0.50 (1:4 ethyl acetate-hexanes); 1H NMR ($CDCl_3$) δ 0.86 (t, 3H, J=6.4 Hz), 1.24-1.32 (m, 24H), 1.60-1.65 (m, 2H), 3.09 (s, 3H), 3.37 (t, 2H, J=7.6 Hz), 6.55 (d, 1H, J=2.8 Hz), 6.68 (d, 1H, J=2.4 Hz), 6.80-6.84 (m, 2H), 7.54 (d, 1H, J=9.6 Hz) and 7.67 (d, 1H, J=9.2 Hz); $^{13}C$ NMR ($CDCl_3$) δ 14.2, 22.6, 27.1, 27.4, 29.50, 29.55, 29.6, 29.7, 29.77, 29.78, 29.81, 29.83, 51.5, 104.8, 113.3, 118.7, 128.7, 131.0, 132.4, 134.8, 136.1, 139.6, 140.2, 150.0 and 182.4; mass spectrum (APCI), m/z 453.2947 (M +($C_{28}H_{41}N_2OS$ requires m/z 453.2940).

Example 5

Synthesis of 7-(N-Butyl-N-pentadecylamino)-3H-phenothiazin-3-one (5)

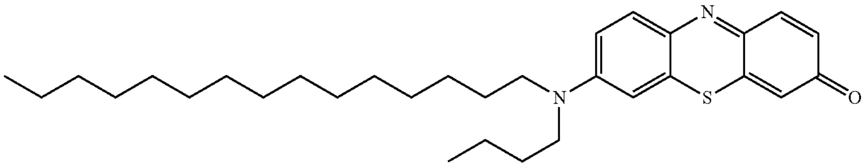 [SMILES: CCCCCCCCCCCCCCCN(CCCC)c1ccc2nc3ccc(=O)cc-3sc2c1]

Step 1. Synthesis of tert-Butyl 3-(N-Butyl-N-pentadecylamino)-7-methoxy-10H-phenothiazin-10-carboxylate (17)

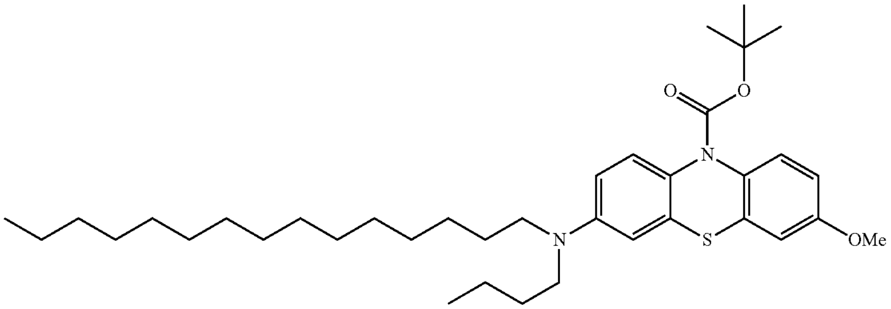 [SMILES: CCCCCCCCCCCCCCCN(CCCC)c1ccc2c(c1)Sc1cc(OC)ccc1N2C(=O)OC(C)(C)C]

0.11 mL (0.14 g, 1.00 mmol) of 1-bromobutane was added into a mixture of 90.0 mg (0.16 mmol) of compound 15 in 2 mL of acetonitrile and 0.17 g (1.60 mmol) of $Na_2CO_3$. The reaction mixture was sealed under nitrogen atmosphere and stirred at 80° C. for ~30 h. The reaction mixture was cooled to room temperature and filtered. The filtrate was concentrated under diminished pressure. The crude product was used to the next step without further purification.

Step 2. Synthesis of 7-(N-Butyl-N-pentadecylamino)-3H-phenothiazin-3-one (5)

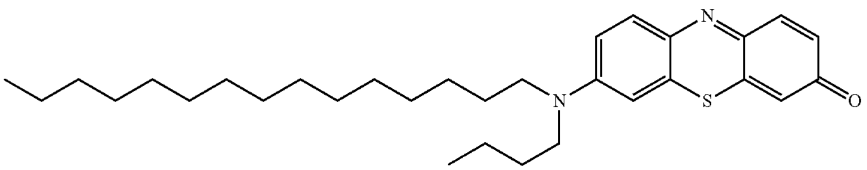 [SMILES: CCCCCCCCCCCCCCCN(CCCC)c1ccc2nc3ccc(=O)cc-3sc2c1]

0.48 mL (0.48 mmol) of 1 M $BBr_3$ in $CH_2Cl_2$ was added dropwise into the solution of 100 mg (~0.16 mmol) of crude 17 in 2 mL of $CH_2Cl_2$ at −78° C. The reaction mixture was stirred overnight at room temperature and was quenched with 10 mL of water. The crude product was extracted with two 10-mL portions of ethyl acetate. The combined organic layer was washed with 20 mL of brine, dried over anhydrous $Na_2SO_4$ and concentrated under reduced pressure. The resulting violet solid was purified on a silica gel column (7×2 cm). Elution with 3:7 ethyl acetate-hexanes afforded 6 as a violet solid: yield 20 mg (25%); silica gel TLC $R_f$ 0.50 (1:4 ethyl acetate-hexanes); 1H NMR ($CDCl_3$) δ 0.88 (t, 3H, J=6.6 Hz), 1.00 (t, 3H, J=7.2 Hz), 1.26-1.43 (m, 26H), 1.62-1.64 (m, 4H), 3.36-3.41 (m, 4H), 6.55 (d, 1H, J=2.4 Hz), 6.71 (s, 1H), 6.79-6.85 (m, 2H), 7.57 (d, 1H, J=9.6 Hz) and 7.68 (d, 1H, J=9.2 Hz); 13C NMR ($CDCl_3$) δ 14.3, 22.8, 27.1, 27.5, 29.50, 29.53, 29.6, 29.7, 29.77, 29.79, 29.81, 29.83, 32.1, 51.5, 104.8, 113.3, 118.7, 128.7, 131.0, 132.4, 134.9, 136.0, 139.6, 140.0, 150.0 and 182.4; mass spectrum (APCI), m/z 495.3330 $(M+H)^+$ ($C_{31}H_{47}N_2OS$ requires m/z 495.3331).

Example 6

Cytotoxicity and Cytoprotection Evaluation

Figure 2:
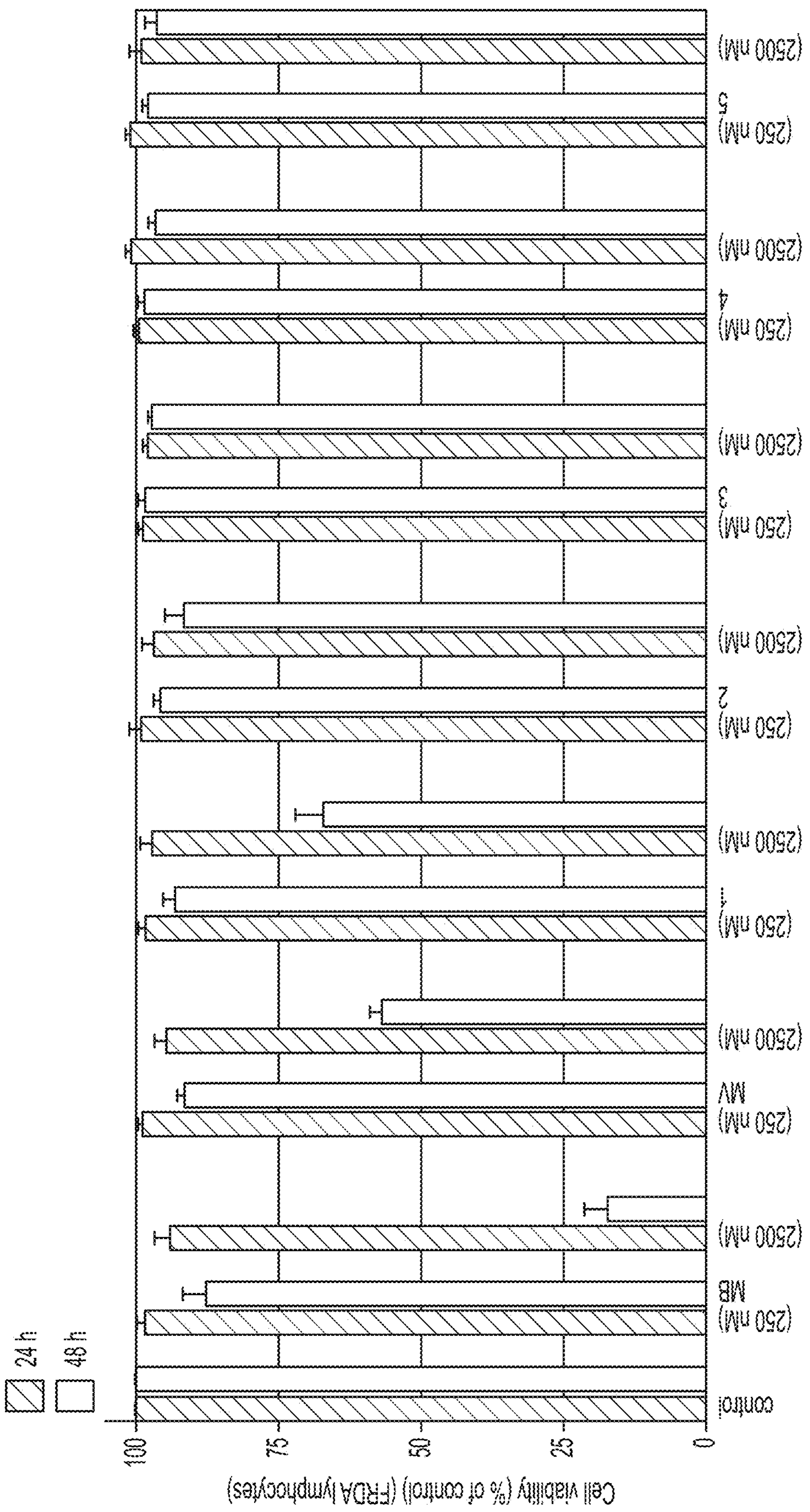
FIG. 2 shows the cytotoxicity of compounds 1-5 on cultured FRDA lymphocytes by incubation for 24 hours or 48 hours in glucose free media (galactose) to force cells to rely on mitochondria to produce their ATP. Flow cytometric determination of cell viability by fluorescence labeling was used employing calcein acetoxy-methyl-ester and ethidium homodimer-1 as live and dead cell stains

Cytotoxicity was assessed by the dye exclusion method. Live cells have intact membranes, which exclude a variety of dyes that easily penetrate the damaged, permeable membranes of non-viable cells. Propidium iodide, a membrane impermeant dye, is generally excluded from viable cells, although it can enter non-viable cells and bind to double-stranded DNA by intercalating between base pairs. Compounds 1-5 were tested for their cytotoxicity in FRDA lymphocytes using FACS analysis with propidium iodide. The results are depicted in FIG. 2. From the results it is evident that cytotoxicity decreases with increasing lipophilicity in lower as well as higher concentrations for compounds 1-5.

Figure 3:
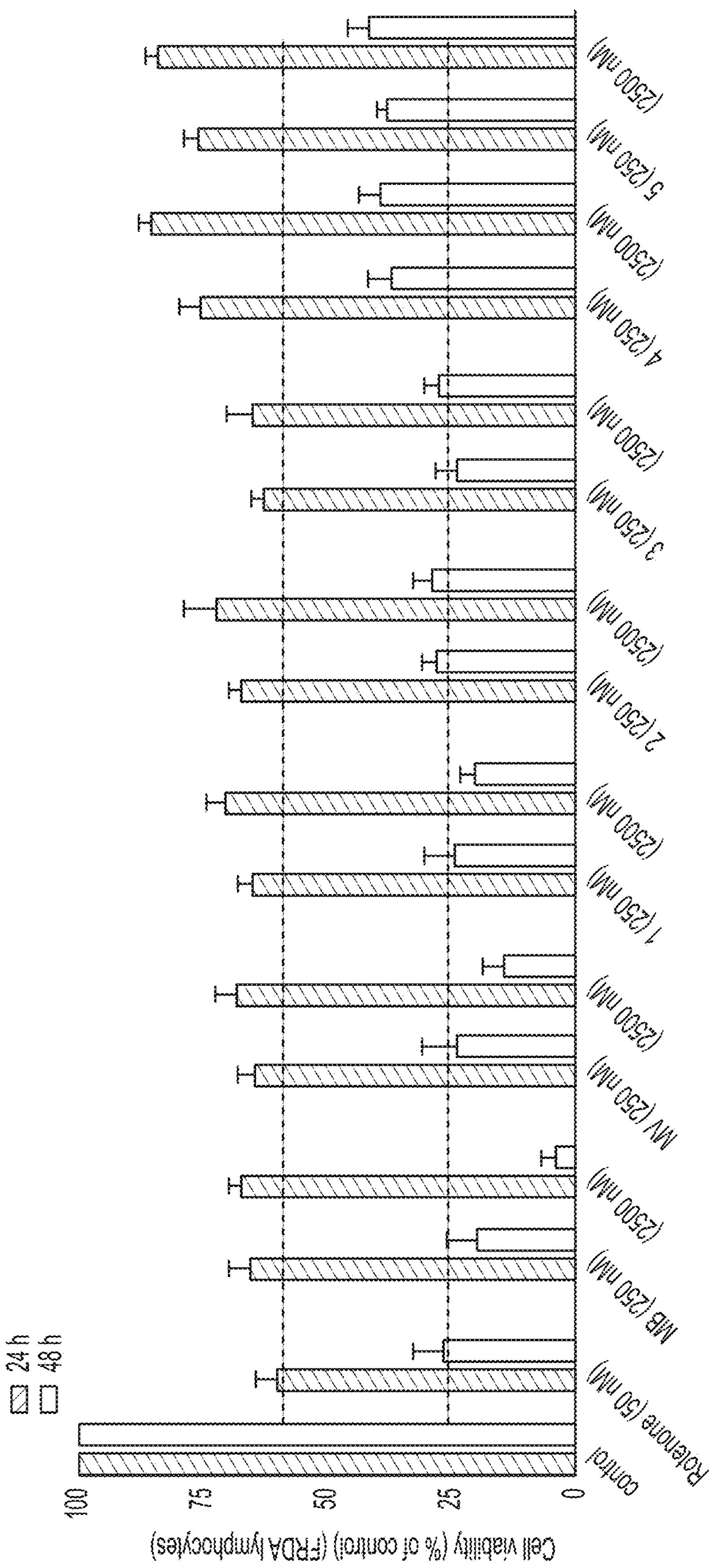
FIG. 3 shows the cytoprotective effect of the test compounds 1-5 in FRDA lymphocytes following preincubation with test compounds for 12 hours in glucose-free media and subsequent treatment with rotenone (50 nM) for 24 hours or 48 hours to inhibit complex I.

The ability of compounds 1-5 to demonstrate cyotoprotection was measured in FRDA lymphocytes. The cells were treated with rotenone to induce cytotoxicity by inhibiting complex I. The results are shown in FIG. 3. Compounds 4 and 5 were able to protect the cells against rotenone cytotoxicity more efficiently than the parent compound MV.

Cytotoxicity Assay

Evaluation of compounds 1-5 for their cytotoxicity and their ability to function within the mitochondrial respiratory chain was carried out by incubation of the prepared compounds for 24 or 48 h with FRDA lymphocytes. A nutrient-sensitized screening strategy has been used by culturing FRDA cells in galactose as the sole sugar source which forces mammalian cells to rely on mitochondrial oxidative phosphorylation (OXPHOS) to produce their ATP; they also become more sensitive to mitochondrial respiratory chain inhibitors than cells grown in glucose medium. Compounds 1-5 were tested for their cytotoxicity in FRDA lymphocytes using a simultaneous staining with a two-color fluorescence assay, the Live/Dead®Viability/Cytotoxicity Kit (Molecular Probes). This assay is used to measure two recognized parameters of cell viability, intracellular esterase activity and plasma integrity. The membrane-impermeant DNA dye ethidium homodimer-1 (EthD-1) was used to identify dead cells whose plasma membrane integrity was disrupted. The membrane-permeant dye calcein-AM was used to label live cells. It penetrates into the cells where it is metabolized by cytoplasmic esterases and becomes a fluorescent but membrane-impermeant probe which is retained in viable cells. One mL of FRDA lymphocyte cells ($5\times10^5$ cells) was plated in a 24-well plate in glucose free media (galactose 25 mM), treated with the test compounds and incubated at 37° C. for 24 h or 48 h in a humidified atmosphere containing 5% $CO_2$ in air. Cells were collected by centrifugation at 300×g for 3 min and washed with phosphate buffered saline. Cells were resuspended in phosphate buffered saline containing 25 mM galactose. Cell suspension was stained with 0.1 μM calcein AM and 0.2 μM EthD-1 and incubated in the dark at 37° C. for 15 minutes. Cells were collected by centrifugation at 300×g for 3 min and then washed with PBS. The samples were analyzed immediately by flow cytometry ($C_6$ Accuri, BD Biosciences, San Jose, CA), using a 488 nm excitation laser and the and the FL1-H channel 530±15 nm emission filter and the FL2-H channel 585±15 nm. For each analysis 10,000 events were recorded and analyzed using $C_6$ Accuri software (BD Biosciences).

Example 7

Preserving Mitochondrial Inner Membrane Potential ($\Delta\Psi_m$)

Figure 4:
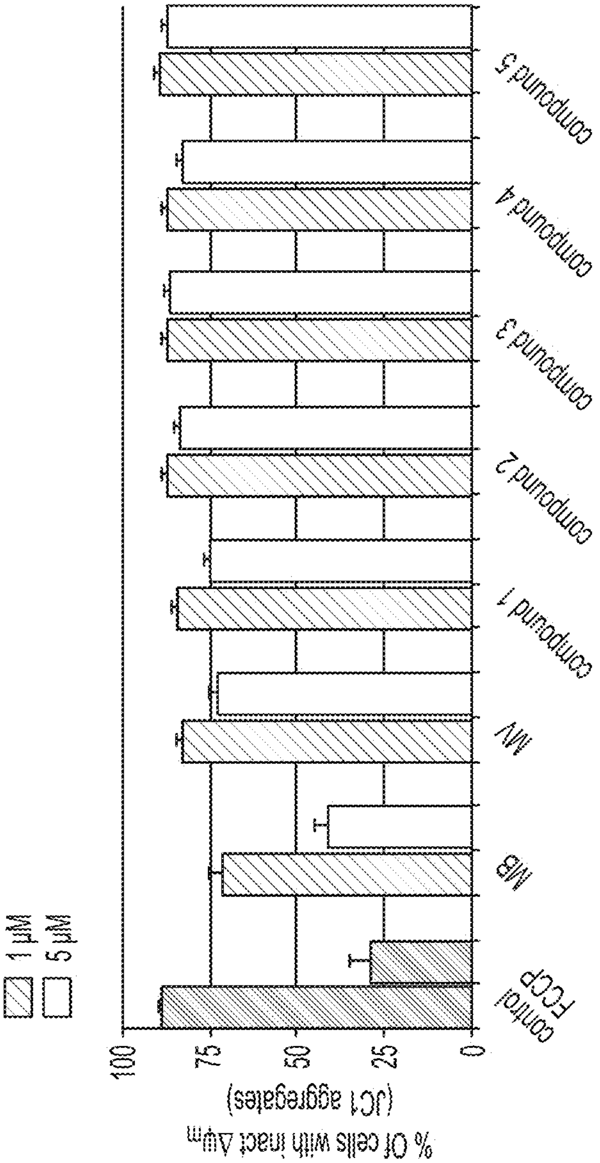
FIG. 4 shows the percentage of cells with intact $\Delta_{\Omega m}$ calculated using Accuri™ $C_6$ software. In each analysis, 10000 events were recorded. Depolarization with carbonyl cyanide p-(trifluoromethoxy) phenylhydrazone (FCCP), was used to serve as a positive control.

The ability of 1-5 to maintain mitochondrial membrane potential ($\Delta\Psi_m$) compared to the parent compound MV was studied. $\Delta\Psi_m$ was determined using the cationic fluorescent dye 5,5',6,6'-tetrachloro-1,1',3,3'-tetraethylbenzimidazolyl carbocyanine iodide (JC-1), which is a lipophilic cation that selectively accumulates in mitochondria due to the negative potential across the inner mitochondrial membrane. The dye exists as a monomer at low concentrations giving a green fluorescence. At higher concentrations the dye forms J-aggregates, which exhibit red fluorescence. Therefore, mitochondrial depolarization is indicated by a decrease in red/green fluorescence ratio. Carbonyl cyanide 4-(trifluoromethoxy)phenylhydrazone (FCCP), a commonly used uncoupler of oxidative phosphorylation in mitochondria, was used as a negative control to dissipate the chemiosmotic proton gradient, which results in depolarization of mitochondrial membrane potential. FIG. 4 summarizes the results of this study. Clearly compounds 2-5 were more effective in preserving mitochondrial membrane potential than the parent compound MV.

JC-1 Mitochondrial Membrane Potential ($\Delta\Psi_m$) Assay

The ability of the test compounds to depolarize or maintains mitochondrial inner membrane potential ($\Delta\Psi_m$) was assessed using the JC-1 probe. JC-1 is a cationic dye which exhibits potential-dependent accumulation in mitochondria. JC-1 is a dual stain, which can identify high membrane potential through J-aggregates (red fluorescence) and low membrane potential through J-monomers (green fluorescence). When the $\Delta\Psi_m$ collapses, the reagent (JC-1) no longer accumulates inside the mitochondria; instead, it is diffuses throughout the cell cytosol in the monomeric form which fluoresces green. The detection of mitochondrial depolarization using JC-lwas accomplished by flow cytometry as described before (Arce et al. (2012) *Bioorg. Med. Chem.*20, 5188). Briefly, FRDA lymphocytes cells ($5\times10^5$ cells) were pre-treated with or without the test compounds for 16 h. The cells were incubated at 37° C. in the dark for 20 min with 1 μM JC-1. Cells were collected by centrifugation at 300×g for 3 min and washed with phosphate buffered saline. Cells were resuspended in phosphate buffered saline supplemented with 20 mM glucose and were analyzed immediately by FACS ($C_6$ Accuri, BD Biosciences, San Jose, CA), using a 488 nm excitation laser and the FL1-H channel 530±15 nm emission filter and the FL2-H channel 585±15 nm. For each analysis 10,000 events were recorded and analyzed using $C_6$ Accuri software (BD Biosciences). FCCP (carbonyl cyanide p-trifluoromethoxyphenyl hydrazone), a mitochondrial uncouple, was used to produce a negative control.

Example 8

Suppression of Reactive Oxygen Species

Figure 5:
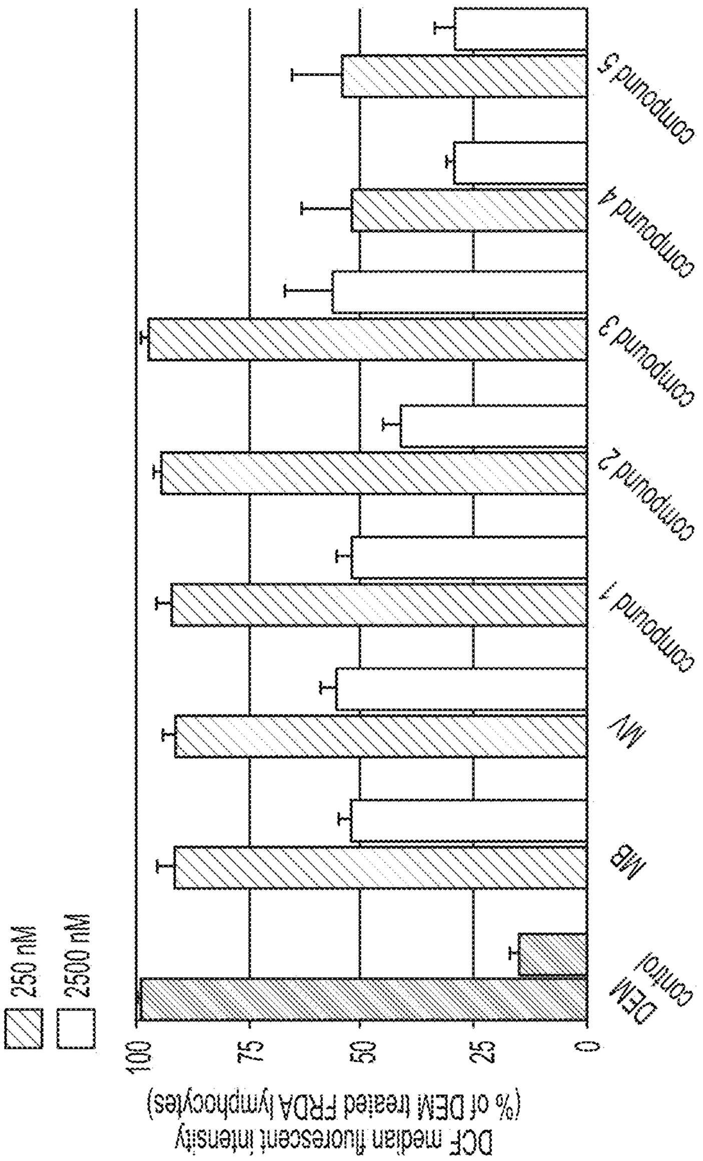
FIG. 5 shows flow cytometric analysis of FRDA lymphocyte cells stained with dichlorodihydrofluorescein diacetate (DCFH-DA) for 20 minutes, following pretreatment with the test compounds 1-5 for 16 hours, and subsequent treatment with diethyl maleate (DEM) for 80 minutes to induce the production of ROS by depleting glutathione.

The ability of compounds 1-5 to suppress ROS induced by the depletion of cellular glutathione was evaluated in FRDA lymphocytes in a quantitative FACS experiment using dichlorofluorescein diacetate (DCFH-DA) as an indicator of intracellular ROS levels. In cells DCFH-DA is hydrolyzed by esterases to afford 2,7-dichlorodihydrofluorescein (DCFH). The non-fluorescent DCFH can be oxidized by cellular oxidants generating fluorescent dichlorofluorescein (DCF). The results are shown in FIG. 5, and demonstrate that compounds 4 and 5 were more potent and effective in protecting FRDA lymphocytes than the parent compound MV and did so in a concentration dependent manner.

Reactive Oxygen Species (ROS) Assay

Intracellular ROS production was measured in FRDA lymphocyte cells (GM15850, Coriell Cell Repositories, Camden, NJ) using the oxidant sensitive fluorescent probe 2,7-dichlorodihydrofluorescein diacetate (DCFH-DA) (Molecular Probes) as described previously. One mL of FRDA lymphocyte cells ($5\times10^5$ cells) was plated in a 24-well plate, treated with the test compounds and incubated at 37° C. for 16 h in a humidified atmosphere containing 5% $CO_2$ in air. Cells were treated with or without 5 mM diethyl maleate (DEM) for 80 min, collected by centrifugation at 300×g for 3 min and then washed with phosphate buffered saline (PBS) (Life Technologies). Cells were resuspended in PBS containing 20 mM glucose and incubated at 37° C. in the dark for 25 min with 10 μM DCFH-DA. Cells were collected by centrifugation at 300×g for 3 min and then washed with PBS. The samples were analyzed immediately by flow cytometry ($C_6$ Accuri, BD Biosciences, San Jose, CA), using a 488 nm excitation laser and the FL1-H channel 530±15 nm emission filter for DCF and FL2-H channel 585±15 nm emission filter for propidium iodide. The generation of ROS, mainly peroxides, was detected as a result of the oxidation of DCFH. In each analysis, 10,000 events were recorded after dead cell and debris were gated out. Apoptotic and dead cells were excluded by using propidium iodide (1 μg/mL) as counter stain dye for nucleic acid. ROS production was evaluated only in living cells which are propidium iodide negative. Propidium iodide is excluded by viable cells but can penetrate cell membranes of dying or dead cells. Results obtained were verified by running duplicates and repeating experiments in three independent runs. Results were expressed as percentage of ROS scavenging activity or as percentage of the median fluorescence intensity of DCF.

Example 9

Determination of ATP Levels

Figure 6:
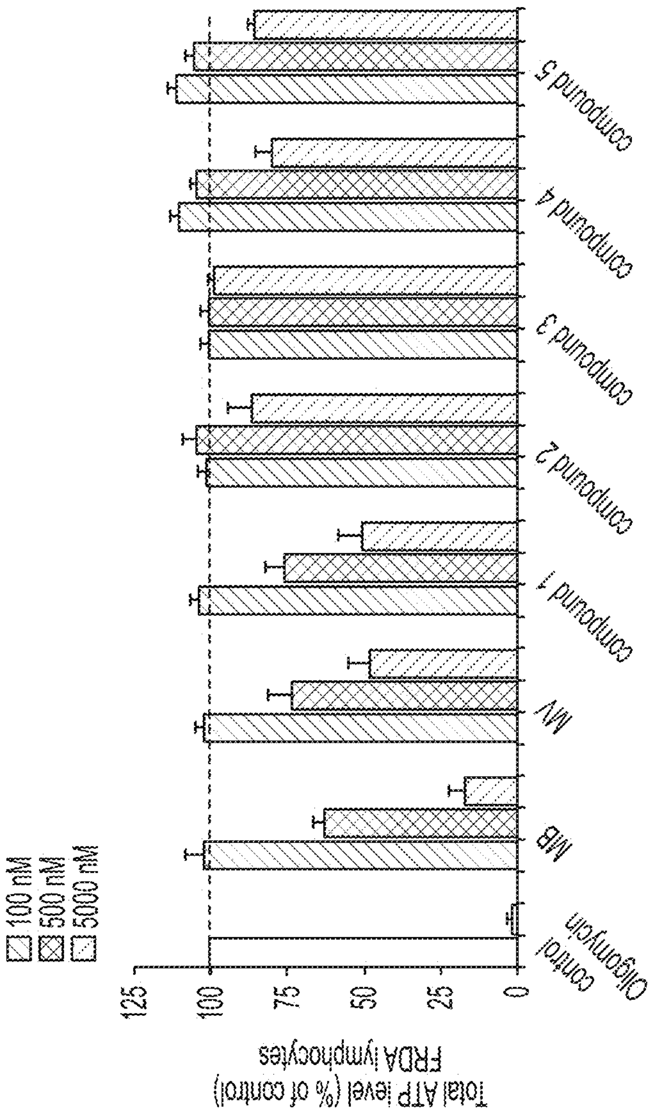
FIG. 6 shows total ATP level in FRDA lymphocytes following incubation with the compounds 1-5 for 24 hours in glucose free media (25 mM galactose). Results are expressed as percentage of total ATP relative to untreated control.

ATP levels in FRDA lymphocytes were measured using firefly luciferase. The cells were grown on glucose-free media supplemented with galactose for 24 h prior to the addition of the test compounds. Since cells grown in galactose rely mostly on oxidative phosphorylation (OX-PHOS) to produce their ATP, they become more sensitive to mitochondrial respiratory chain inhibitors than cells grown in glucose medium. The results are shown in FIG. 6. MV strongly reduces cellular ATP levels in a concentration dependent manner. Compounds 1 and 2 reduces cellular ATP levels in all concentrations. Compounds 3-5 maintain ATP levels up to 2.5 μM concentration, beyond that they reduce ATP levels significantly.

Measurement of Cellular ATP Concentration

Total ATP levels in FRDA lymphocytes with or without partially blocking complex I activity with rotenone (5 nM) were measured using firefly luciferase as a means to measure ATP level. The cells were grown on glucose-free media supplemented with galactose. Since cells grown in galactose rely mostly on oxidative phosphorylation (OXPHOS) to produce their ATP, they become more sensitive to mitochondria respiratory chain inhibitors than cells grown in glucose medium. Briefly, lymphocytes ($2\times10^5$ce11/mL) were plated (1 mL) in 24-well plates, treated with the test compounds, and then incubated at 37° C. for 48 h in a humidified atmosphere containing 5% $CO_2$ in air. FRDA lymphocytes with partial inhibition of complex I, cells were preincubated with test compounds for overnight before rotenone (5 nM) treatment for 24 h. Cells in each well were mixed and transferred (100 μL) to 96-well microtiter black-walled cell culture plates (Costar, Corning, NY). The total intracellular ATP level was measured in a luminator (Clarity™ luminescence microplate reader) using an ATP Bioluminescence Assay Kit (ViaLight®-Plus ATP monitoring reagent kit, Lonza) following the manufacturer's protocol. The total ATP level was expressed as a percentage of untreated control. Data are reported as the mean of at least three independent experiments.

Example 10

Figure 7:
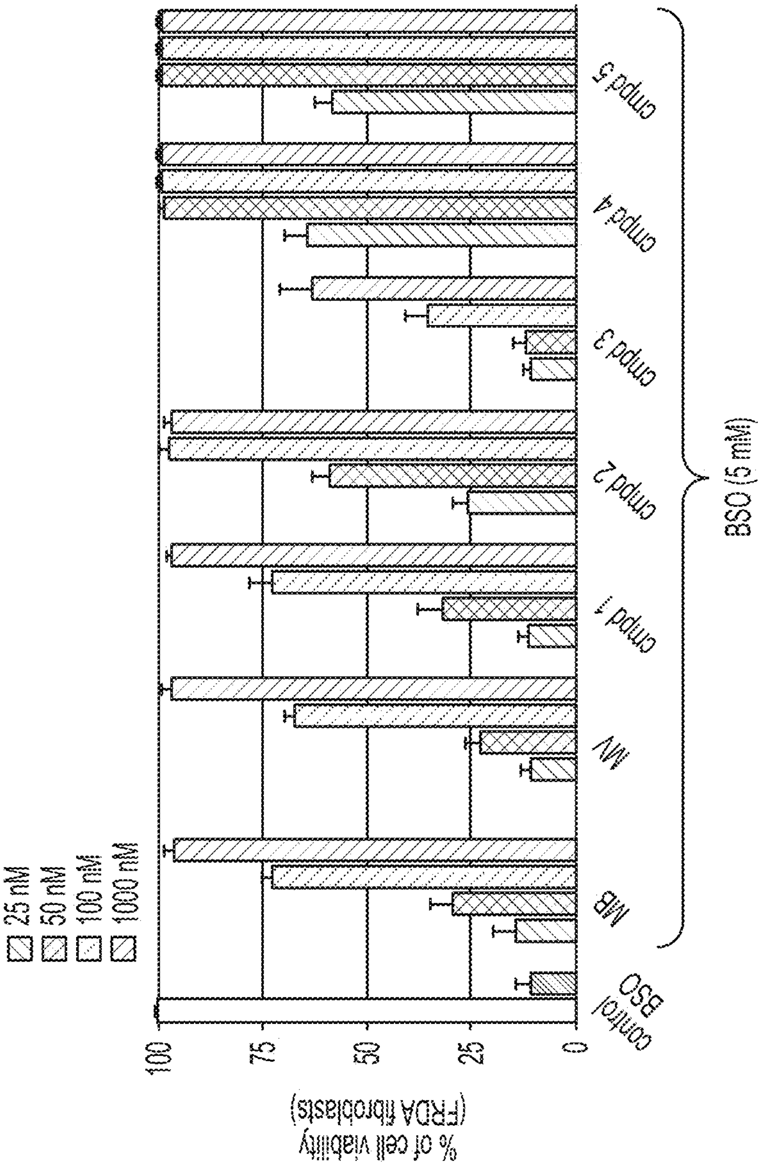
FIG. 7 shows the cytoprotective effect of compounds 1-5 in (BSO)-treated FRDA fibroblasts following preincubation with test compounds and subsequent treatment with BSO (5 mM) for 48 h. Results obtained were verified by running triplicates and repeating experiments in two independent runs.

Methylene Violet Analogues as Mitochondrial Therapeutic Agents (a) Cytoprotective effect of compounds 1-5 in (BSO)-treated FRDA fibroblasts (FIG. 7).

The ability of test compounds 1-5 to confer cytoprotection to buthionine sulfoximine (BSO)-treated FRDA fibroblasts from oxidative damage-induced death was determined by using simultaneous staining with a two-color fluorescence assay, the Live/Dead® Viability/Cytotoxicity Kit (Molecular Probes, Eugene, OR). The cells were subjected to L-buthionine (S,R)-sulfoximine, an inhibitor of de novo glutathione (GSH) biosynthesis. Oxidative damage-induced death of FRDA fibroblasts was blocked by the test compounds in a concentration dependent manner (FIG. 7). Compounds 4 and 5, each having a single longer alkyl substituent, exhibited better potency than 1 or 2 and were by far the most efficient when tested at lower concentrations. The optimal side chain length was 15 carbon atoms. Interestingly, compound 3, having two 15-carbon substituents, was the least effective in this assay.

Detailed Method

The ability of the test compounds to confer cytoprotection to BSO-treated FRDA fibroblasts was determined by assessing plasma membrane integrity and intracellular esterase activity using the LIVE/DEAD Viability/Cytotoxicity Kit for mammalian cells according to the manufacturer's protocol. Briefly, FRDA fibroblasts (GM04078) were plated in 96-well microtiter plates at a density of 3000 cell/well (50 μL) (Costar, Corning, NY). The plates were incubated at 37° C. for 24 h in an atmosphere having 95% humidity and 5% $CO_2$ to allow attachment of the cells to the culture plates and to allow the cell density reach 50-60% confluency. The next day the test compounds were dissolved in DMSO, diluted to the appropriate concentrations in fresh cell culture media and the cells were then treated with the test compounds (final DMSO concentration was <0.5%). Plates were incubated at 37° C. overnight in a humidified atmosphere containing 5% $CO_2$ in air. The following day BSO solution (in culture media) was added to each well to achieve a final BSO concentration of 5 mM. After 48 hours of BSO treatment, the media was removed, and cells were stained with the Live/Dead® reagent (4 μM ethidium bromide homodimer, 1.2 μM calcein-AM) and then incubated at 37° C. for 60 min in the dark to allow the dye to enter the cell and be hydrolyzed by esterases. Fluorescence intensities were measured with a Spectramax M5 spectrofluorometer (Molecular Devices, Sunnyvale, CA) using excitation and emission wavelengths of 485 nm and 525 nm, respectively. The test compounds were assayed in triplicate. The viability of non-BSO treated fibroblasts was set as 100%, and the viability of the BSO treated and sample-treated cells was calculated relative to this value. Cell viability was expressed as the percentage of control.

Figure 8:
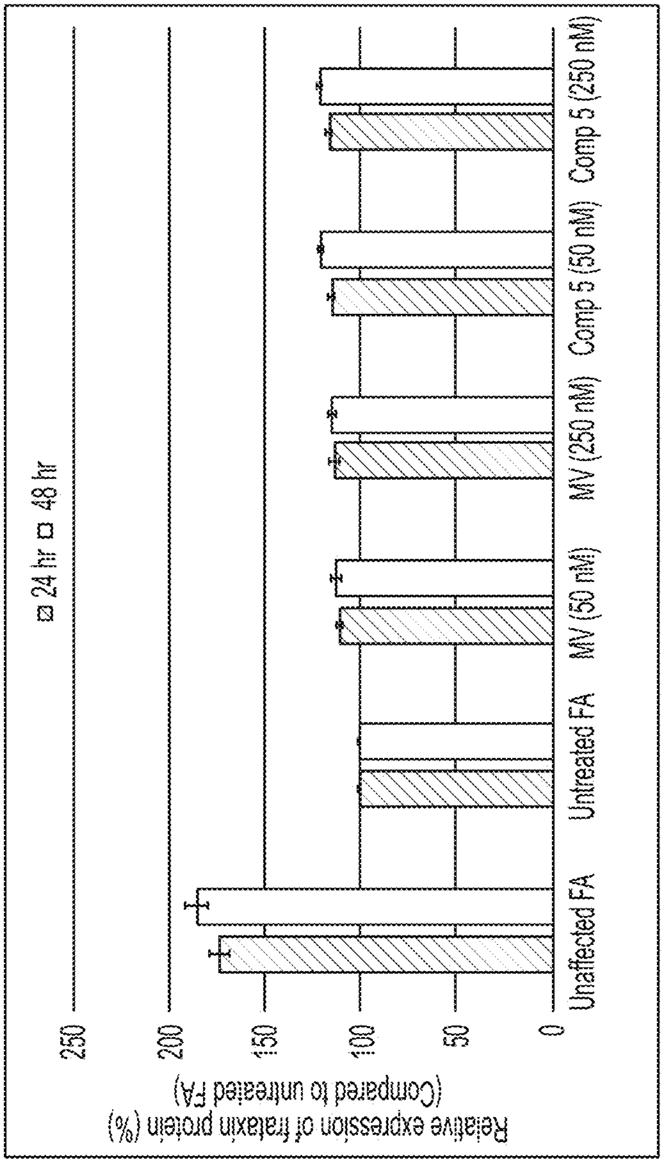
FIG. 8 shows the effect of methylene violet analogue on frataxin expression level in Friedreich ataxia cells determined by an enzyme-linked immunosorbent assay following 24 and 48 hours of treatment. In-Cell ELISA Kits were used to assess protein levels of frataxin.
Figure 9:
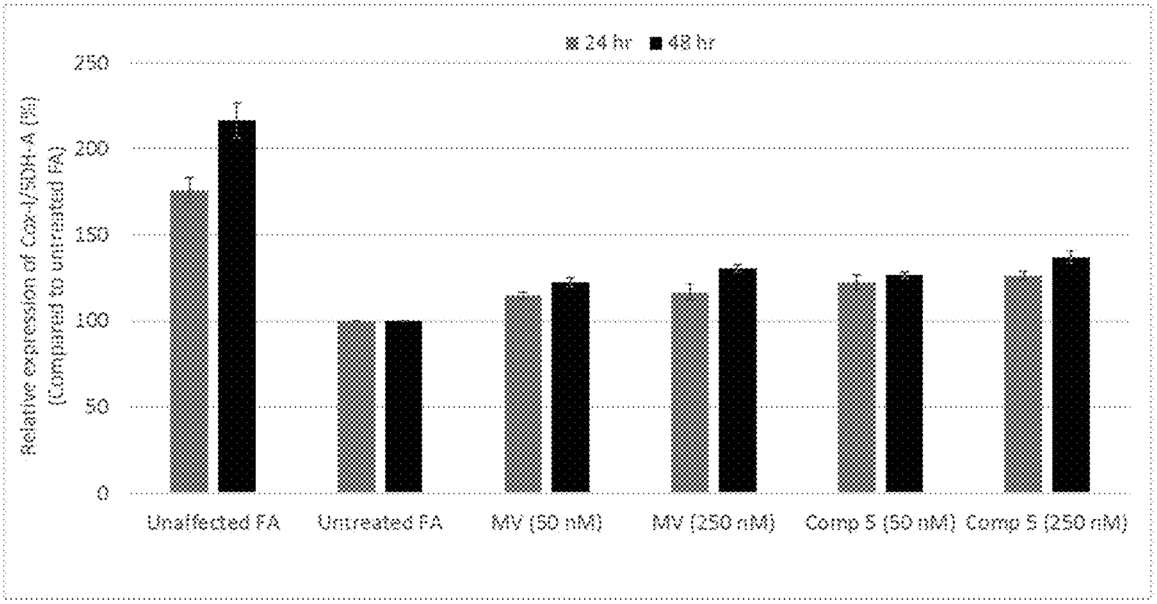
FIG. 9 shows the effect of methylene violet analogue on mitochondrial biogenesis in Friedreich ataxia cells determined by an enzyme-linked immunosorbent assay following 24 and 48 hours of treatment. In-Cell ELISA Kits was used to assess protein levels of succinate dehydrogenase (SDH-A), a subunit of complex II (nDNA-encoded protein) and cytochrome c oxidase subunit 1 (COX-1), a subunit of complex IV (mtDNA-encoded). Interpretation: Higher the ratio of COX-I/SDH-A (%) indicated increases mitochondrial biogenesis due to mitochondrial DNA-encoded COX-I protein synthesis is higher as compared to nuclear DNA-encoded SDH-A protein.

(b) Effect of methylene violet analogue on frataxin expression level and on mitochondrial biogenesis in Friedreich ataxia cells (FIGS. 8 and 9).

Method:

Cell lines and culture conditions:

Human Friedreich's ataxia affected B-lymphocytes cell line (cat#: GM16216) and clinically unaffected Friedreich's ataxia B-lymphocytes cell line (cat#: GM16213) were obtained from Coriell Cell Repositories (Camden, NJ). Lymphocytes were routinely cultured in RPMI-1640 medium (Gibco, Life Technologies, Grand Island, NY) with added 15% fetal calf serum (FBS) and 1% penicillin—streptomycin antibiotic supplement (Cellgro, Manassas, VA). Cells were passaged every other day to maintain them in log phase growth and kept at a nominal concentration range of $5\text{-}10\times10^5$. Treatment and measurements of Frataxin level and mitochondrial biogenesis:

Lymphocytes were seeded at density of $5\times10^5$ cell/mL in 24-well plate and treated with the test compounds and incubated at 37° C. for 24 and 48 hr in a humidified atmosphere containing 5% $CO_2$ in air. After treatment period, frataxin levels were measured using the Frataxin Human Simple Step enzyme-linked immunosorbent assay (ELISA) kit (cat#: ab176112, Abcam, UK) according to manufacturer's protocol. For mitochondrial biogenesis, the treated suspension lymphocytes cells were then transferred to the amine assay plate (cat#354717, Corning, USA) and follow immediately the fixation step and quantitative immunocytochemistry assay to measure protein levels of succinate dehydrogenase (SDH-A), a subunit of complex II (nuclear DNA-encoded protein) and cytochrome c oxidase subunit 1 (COX-1), a subunit of complex IV (mitochondrial DNA-encoded) according to protocol describe in In-Cell mitochondrial biogenesis ELISA Kit (cat#: ab110217, Abcam, UK).

Example 11

The following illustrate representative pharmaceutical dosage forms, containing a compound of formula I (compound X), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X- | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

-continued

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Discussion

Compounds 1-5 were synthesized using the Smiles rearrangement where functionalized phenothiazines are prepared by the intramolecular rearrangement of functionalized diphenyl sulfides under basic conditions (Schemes 1 and 2). The diphenyl sulfide intermediate 7 was prepared by the coupling of 2-amino-5-methoxybenzothiol and 2, 4-dinitrochlorobenzene under mildly acidic condition. The highly unstable 2-amino-5-methoxybenzothiol was prepared by the basic hydrolysis of 2-amino-5-methoxybenzothiazole at reflux (Arce, P. M. et al. *ACS Med Chem. Lett.* 2011, 2, 608). The thiol was used for the coupling step without isolation or further purification from the reaction mixture. The high yield of 7 (81%) indicates the efficient formation of the thiol intermediate. Compound 7 was then activated as its acetamide derivative (8) by treatment with acetic anhydride. Smiles rearrangement of 8 under mildly basic condition yielded the functionalized phenothiazine 9 in 90% yield. Subsequently the nitro group at position 7 was reduced to afford an aromatic amine, which was alkylated using different alkyl iodides/bromides under basic conditions to obtain compounds 12-17. Removal of the Boc and methyl groups by $BBr_3$ afforded the final compounds 1-5 in varying yields.

A number of representative compounds of formula I have been designed and synthesized with variations in their redox core and their side chain that could enable the compounds to protect against oxidative stress, augment ATP levels and enhance mitochondrial function. The strong cytotoxicity of MB itself in FRDA lymphocytes at 0.5-2.5 concentrations was surprising, given its long clinical use. A nutrient-sensitized screening strategy was used by culturing the FRDA cells on galactose as the sole sugar source, forcing them to rely on mitochondrial OX-PHOS to produce their ATP; consequently they became more sensitive to respiratory chain inhibitors than cells grown on glucose. FIG. 2 shows that MB was cytotoxic when used at 2.5 μM concentration for 48 h. The compounds of formula I with long alkyl side chains (3-5) were not significantly cytotoxic under any tested condition, although compounds of formula I with shorter side chains (1 and 2) were somewhat cytotoxic. Shown in FIG. 5 are the abilities of the compounds of formula I to suppress ROS production in FRDA lymphocytes depleted of glutathione by using 5 mM diethyl maleate. The compounds of formula I preserved the mitochondrial membrane potential of FRDA lymphocytes. FACS analysis of $\Delta\Psi_m$ showed that MB and MV significantly depolarized $\Delta\Psi_m$, while compounds of formula I did not (FIG. 4). The three long alkyl chain compounds of formula I also restored ATP levels in FRDA lymphocytes (FIG. 6). In contrast, MB itself inhibited ATP production, especially at higher concentrations. The side chain modifications also had a dramatic effect on their ability to afford cytoprotection to rotenone-treated FRDA lymphocytes (FIG. 3).

In conclusion, five representative compounds of formula I were designed and synthesized. The synthetic route involved Smiles rearrangement as one of the key steps to obtain a substituted phenothiazine compounds. The yields for the final compounds ranged from 25-50% with high purity. When the compounds were tested for their ability to act as multifunctional radical quenchers in FRDA lymphocytes they exhibit better antioxidant activity than MB and MV compounds.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of preserving mitochondrial function in an animal comprising administering to the animal an effective amount of compound of formula (I);

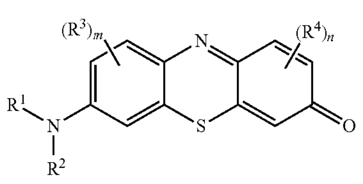

I or pharmaceutically acceptable salt thereof, wherein:

$R^1$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN;

$R^2$ is $C_{1-20}$ alkenyl, $C_{2-20}$ alkynyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN; or $R^1$ and $R^2$ taken together with the nitrogen to which they are attached form a 3-12 membered heterocycle that is optionally substituted with one or more groups independently selected from $C_{1-4}$ alkyl, $C_{1-4}$ haloalkyl, —F, —Cl, —Br, —I, —$OR^a$, —$SR^a$, —$NR^aR^b$, oxo, —$NO_2$ and —CN;

each $R^3$ is independently selected from the group consisting of —F, —Cl, —Br, —I, —OH, —$OR^a$, —$SR^a$, —$NR^aR^b$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^4$ is independently selected from the group consisting of —F, —Cl, —Br, —I, —$OR^a$, —$SR^a$, —$NR^aR^b$, —$NO_2$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl;

each $R^b$ is independently hydrogen or $C_{1-4}$ alkyl;

the subscript m is 0, 1, 2 or 3; and the subscript n is 0, 1, 2, or 3.

2. A method of protecting cells from oxidative stress in an animal comprising administering to the animal an effective amount of compound of formula (I);

I

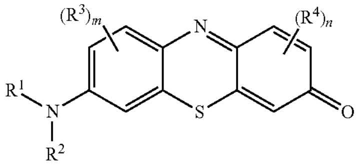

or pharmaceutically acceptable salt thereof, wherein:

$R^1$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN;

$R^2$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN; or $R^1$ and $R^2$ taken together with the nitrogen to which they are attached form a 3-12 membered heterocycle that is optionally substituted with one or more groups independently selected from $C_{1-4}$ alkyl, $C_{1-4}$ haloalkyl, —F, —Cl, —Br, —I, —OH, —$OR^a$, —$SR^a$, —$NR^aR^b$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently; selected from —F, —Cl, —Br, —I, —$OR^a$, —$SR^a$, —$NR^aR^b$, oxo, —$NO_2$ and —CN;

each $R^3$ is independently selected from the group consisting of —F, —Cl, —Br, —I, —OH, —$OR^a$, —$SR^a$, —$NR^aR^b$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^4$ is independently selected from the group consisting of —F, —Cl, —Br, —I, —$OR^a$, —$SR^a$, —$NR^aR^b$, oxo, —$NO_2$ and —CN; $C_{1-4}$ alkyl, $C_{2-4}$ alkenyl and $C_{2-4}$ alkynyl, and wherein the $C_{1-4}$ alkyl: $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl;

each $R^b$ is independently hydrogen or $C_{1-4}$ alkyl;

the subscript m is 0, 1, 2 or 3; and the subscnpt n is 0, 1, 2, or 3.

3. A method of preserving mitochondrial membrane potential and/or augmenting ATP production in an animal comprising administering to the animal an effective amount of compound of formula (I);

I

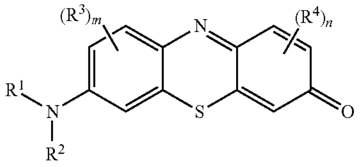

or pharmaceutically acceptable salt thereof, wherein:

$R^1$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN;

$R^2$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN; or $R^1$ and $R^2$ taken together with the nitrogen to which they are attached form a 3-12 membered heterocycle that is optionally substituted with one or more groups independently selected from $C_{1-4}$ alkyl, $C_{1-4}$ haloalkyl. —F, —Cl, —Br, —I, —$OR^a$, —$SR^a$, —$NR^aR^b$, oxo, —$NO_2$ and —CN;

each $R^3$ is independently selected from the group consisting of —F, —Cl, —Br, —I, —OH, —$OR^a$, —$SR^a$, —$NR^aR^b$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^4$ is independently selected from the group consisting of —F, —Cl, —Br, —I, —$OR^a$, —$SR^a$, —$NR^aR^b$, oxo, —$NO_2$ and —CN; $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl;

each $R^b$ is independently hydrogen or $C_{1-4}$ alkyl;

the subscript m is 0, 1, 2 or 3; and the subscript n is 0, 1, 2, or 3.

4. A method of preserving mitochondrial membrane potential and/or augmenting ATP production of a cell in vitro comprising contacting the cell with an effective amount of compound of formula (I);

I

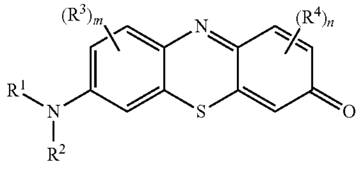

or pharmaceutically acceptable salt thereof, wherein:

$R^1$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN;

$R^2$ is $C_{1-20}$ alkyl, $C_{2-20}$ alkenyl or $C_{2-20}$ alkynyl, and wherein the $C_{1-20}$ alkyl, $C_{2-20}$ alkenyl and $C_{2-20}$ alkynyl are optionally substituted with one or more groups independently selected from —F, —Cl, —Br, —I, —$OR^a$, —$SR^a$, —$NR^aR^b$, oxo, —$NO_2$ and —CN; or $R^1$ and $R^2$ taken together with the nitrogen to which they are attached form a 3-12 membered heterocycle that is optionally substituted with one or more groups independently selected from $C_{1-4}$ alkyl, $C_{1-4}$ haloalkyl. —F, —Cl, —Br, —I, —$OR^a$, —$SR^a$, —$NR^aR^b$, oxo, —$NO_2$ and —CN;

each $R^3$ is independently selected from the group consisting of —F, —Cl, —Br, —I, —OH, —$OR^a$, —$SR^a$, —$NR^aR^b$, —CN, $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^4$ is independently selected from the group consisting of —F, —Cl, —Br, —I, —$OR^a$, —$SR^a$, —$NR^aR^b$, oxo, —$NO_2$ and —CN; $C_{1-4}$ alkyl, $C_{2-4}$ alkenyl and $C_{2-4}$ alkynyl, and wherein the $C_{1-4}$ alkyl, $C_{2-4}$ alkenyl and $C_{2-4}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl;

each $R^b$ is independently hydrogen or $C_{1-4}$ alkyl;

the subscript m is 0, 1, 2 or 3; and the subscript n is 0, 1, 2, or 3.

5. The method of claim 1, wherein the compound of formula I is compound of formula Ia:

Ia

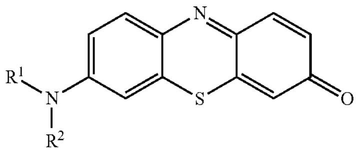

or a pharmaceutically acceptable salt thereof.

6. The method of claim 2, wherein the compound of formula I is a compound of formula Ia:

Ia

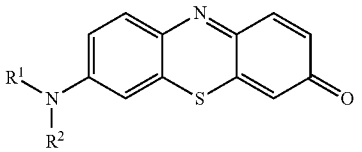

or a pharmaceutically acceptable salt thereof.

7. The method of claim 3, wherein the compound of formula I is a compound of formula Ia:

Ia

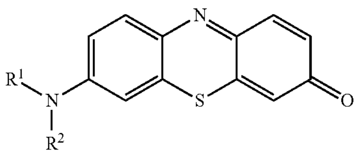

or a pharmaceutically acceptable salt thereof.

8. The method of claim 4, wherein the compound of formula I is a compound of formula Ia:

Ia

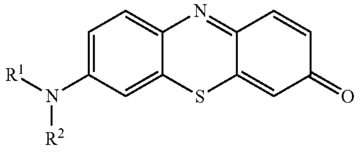

or a pharmaceutically acceptable salt thereof.

9. The method of claim 1, wherein $R^1$ is $C_{1-20}$ alkyl and $R^2$ is $C_{1-20}$ alkyl.

10. The method of claim 2, wherein $R^1$ is $C_{1-20}$ alkyl and $R^2$ is $C_{1-20}$ alkyl.

11. The method of claim 3, wherein $R^1$ is $C_{1-20}$ alkyl and $R^2$ is $C_{1-20}$ alkyl.

12. The method of claim 4, wherein $R^1$ is $C_{1-20}$ alkyl and $R^2$ is $C_{1-20}$ alkyl.

13. The method of claim 1, wherein $R^1$ is $C_{12-20}$ alkyl, $C_{12-20}$ alkenyl or $C_{12-20}$ alkynyl, and wherein the $C_{12-20}$ alkyl, $C_{12-20}$ alkenyl and $C_{12-20}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl; and each $R^b$ is independently hydrogen or $C_{1-4}$ alkyl.

14. The method of claim 2, wherein $R^1$ is $C_{12-20}$ alkyl, $C_{12-20}$ alkenyl or $C_{12-20}$ alkynyl, and wherein the $C_{12-20}$ alkyl, $C_{12-20}$ alkenyl and $C_{12-20}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl; and each $R^b$ is independently hydrogen or $C_{1-4}$ alkyl.

15. The method of claim 3, wherein $R^1$ is $C_{12-20}$ alkyl, $C_{12-20}$ alkenyl or $C_{12-20}$ alkynyl, and wherein the $C_{12-20}$ alkyl, $C_{12-20}$ alkenyl and $C_{12-20}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl; and each $R^b$ is independently hydrogen or $C_{1-4}$ alkyl.

16. The method of claim 14, wherein $R^1$ is $C_{12-20}$ alkyl, $C_{12-20}$ alkenyl or $C_{12-20}$ alkynyl, and wherein the $C_{12-20}$ alkyl, $C_{12-20}$ alkenyl and $C_{12-20}$ alkynyl are optionally substituted with one or more groups independently selected from —F, —Cl, —Br, —I, —$OR^a$, —$SR^a$, —$NR^aR^b$, oxo, —$NO_2$ and —CN;

each $R^a$ is independently hydrogen or $C_{1-4}$ alkyl; and each $R^b$ is independently hydrogen or $C_{1-4}$ alkyl.

17. The method of claim 1, wherein the compound of formula I is selected from the group consisting of:

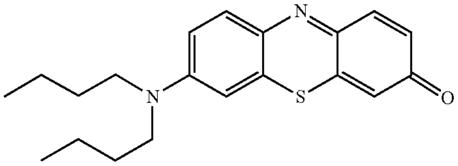
1
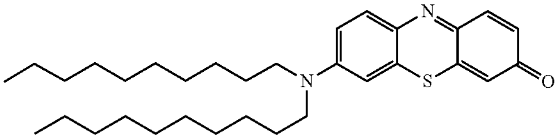
2
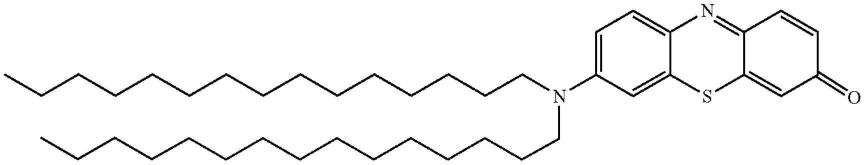
3
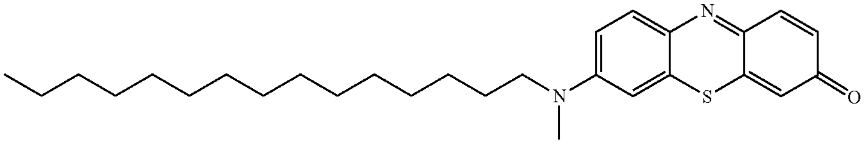
4
and
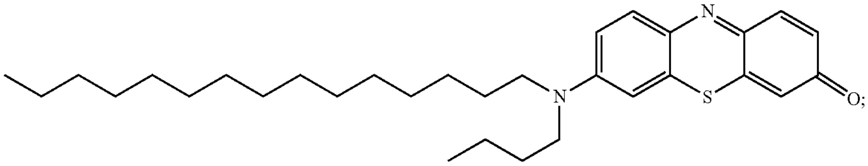
5
and pharmaceutically acceptable salts thereof.
18. The method of claim 2, wherein the compound of formula I is selected from the group consisting of:
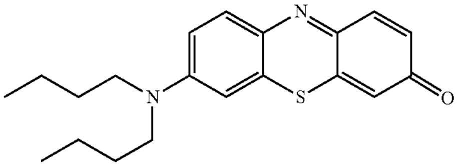
1
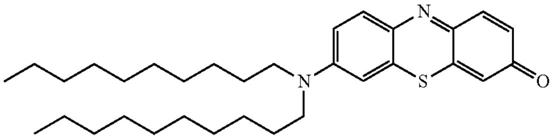
2
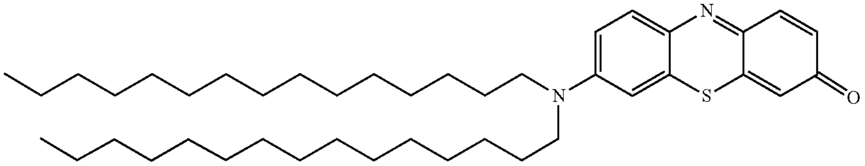
3
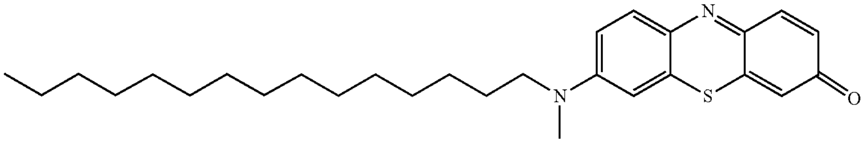 and
4

-continued
5
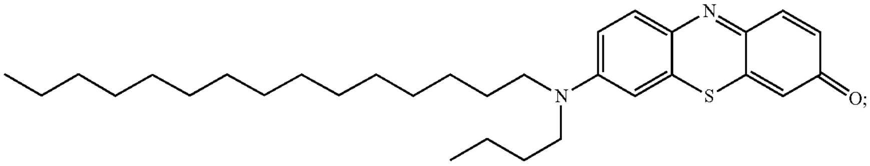
and pharmaceutically acceptable salts thereof.
19. The method of claim 3, wherein the compound of formula I is selected from the group consisting of:
1
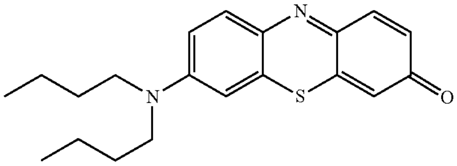
2
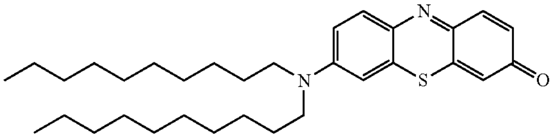
3
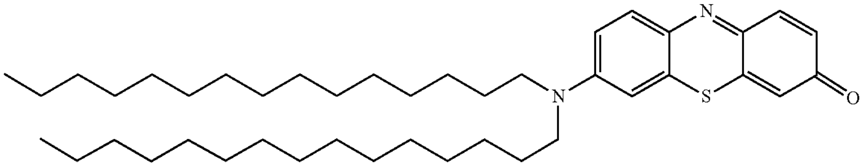
4
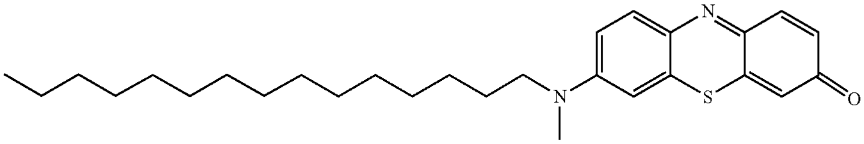
and
5
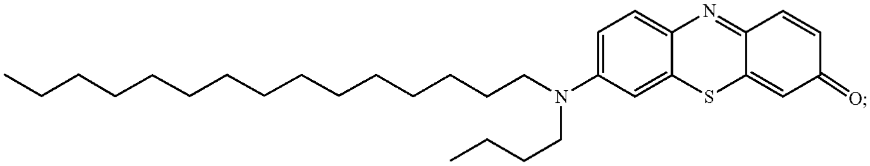
and pharmaceutically acceptable salts thereof.
20. The method of claim 4, wherein the compound of formula I is selected from the group consisting of:
1
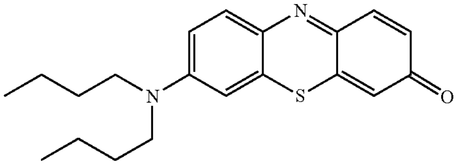
2
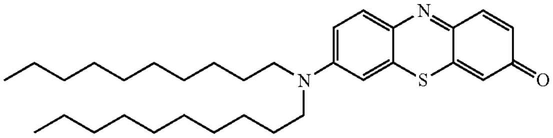
3
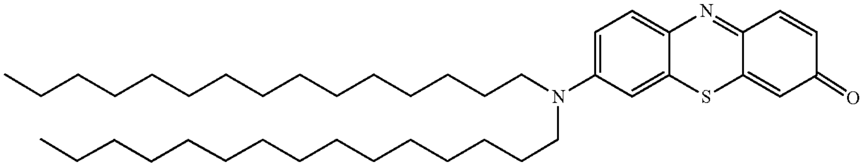

-continued
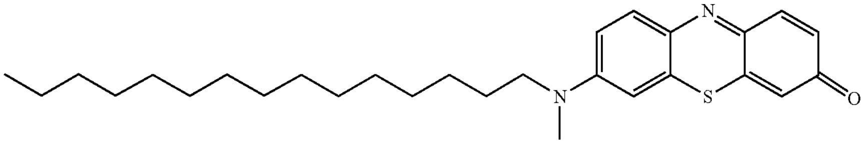
4
and
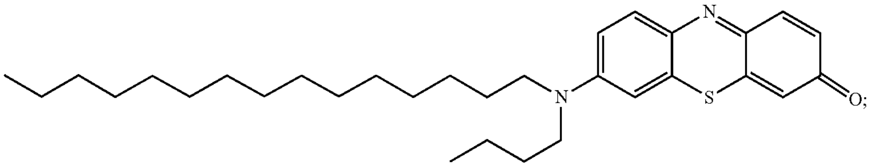
5
;
and pharmaceutically acceptable salts thereof.
* * * * *